(12) United States Patent
Sayer et al.

(10) Patent No.: US 11,279,976 B2
(45) Date of Patent: *Mar. 22, 2022

(54) MAJOR HISTOCOMPATIBILITY COMPLEX SINGLE NUCLEOTIDE POLYMORPHISMS

(71) Applicant: Illumina, Inc., San Diego, CA (US)

(72) Inventors: David Charles Sayer, East Fremantle (AU); Hayley Marianne Hogan, Maylands (AU); Karolina Mercoulia, Shenton Park (AU)

(73) Assignee: Illumina, Inc., San Diego, CA (US)

( * ) Notice: Subject to any disclaimer, the term of this patent is extended or adjusted under 35 U.S.C. 154(b) by 107 days.

This patent is subject to a terminal disclaimer.

(21) Appl. No.: 16/362,310

(22) Filed: Mar. 22, 2019

(65) Prior Publication Data
US 2019/0264282 A1    Aug. 29, 2019

Related U.S. Application Data

(63) Continuation of application No. 15/029,224, filed as application No. PCT/AU2014/000980 on Oct. 15, 2014, now Pat. No. 10,280,461.

(30) Foreign Application Priority Data

Oct. 15, 2013  (AU) .................... 2013903971

(51) Int. Cl.
| C12Q 1/68 | (2018.01) |
| C12Q 1/6881 | (2018.01) |
| C12Q 1/6883 | (2018.01) |
| G01N 27/447 | (2006.01) |

(52) U.S. Cl.
CPC ......... *C12Q 1/6881* (2013.01); *C12Q 1/6883* (2013.01); *G01N 27/447* (2013.01); *C12Q 2600/106* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 6,500,614 B1 * | 12/2002 | Arguello | .............. | C12Q 1/6827 536/23.1 |
| 2005/0266432 A1 | 12/2005 | Oliphant | | |
| 2008/0182252 A1 | 7/2008 | Antovich | | |
| 2008/0261205 A1 * | 10/2008 | Denomme | .............. | C07H 21/04 435/6.16 |

FOREIGN PATENT DOCUMENTS

| KR | 20090051803 | 5/2018 |
| WO | WO 2002/018414 | 3/2002 |
| WO | WO 2012/080359 | 6/2012 |
| WO | WO 2015/054731 A1 | 4/2015 |
| WO | WO 2015/085350 | 6/2015 |

OTHER PUBLICATIONS

Petersdorf et al. ((2007) MHC haplotype matching for unrelated hematopoietic cell transplantation. PLoS Med 4(1): e8. doi:10.1371/journal.pmed.0040008, 10 pages).*
Delgi-Esposti et al. (Human Immunology 34, 242-252 (1992)).*
Alper et al. (Exp Clin Immunogenet 1992 9:58-71).*
Chung et al. (Am. J. Hum. Genet. 71:810-822, 2002).*
Wu et al. (Cytogenet Genome Res 123:131-141 (2008)).*
Moyer et al. (Human Immunology 79(2018) 532-536).*
Clancey et al. (Biol Blood Marrow Transplant 25(2019)891-898).*
Askar et al. (Biol Blood Marrow Transplant. 25(2019)664-672).*
Hogan et al. Tissue Antigens, 2013, 81, 291-292, abstract O67.*
"[HG-U133_Plus_2] Affymetrix Human Genome U133 Plus 2.0 Array", Nov. 7, 2003 (Nov. 7, 2003), XP055381695, Retrieved from the Internet: URL:https://www.ncbi.nlm.nih.gov/geo/query/acc.cgi?acc=GPL570 [retrieved on Jun. 14, 2017].
Alper, C.A., et al., Conserved, extended MHC haplotypes, Experimental Clinical Immunogenetics 9:58-71 (1992).
Awdeh, Z L., et al., Predictability of alloreactivity among unrelated individuals, Tissue Antigens 39:51-57 (1992).
Blanchong, C. et al., "Genetic, structural and functional diversities of human complement components C4A and C4B and their mouse homologues, Slp and C4.", International Immunopharmacology, vol. 1 (3), Mar. 2001, 365-392.
Chung, E.K., et al, Determining the one, two, three, or four long and short loci of human complement C4 in major histocompatibility complex haplotype encoding C4A or C4B proteins, Am J Human Genetics, 71:810-822 (2002).
Dorak, M.T., et al., MHC class III polymorphisms in selection of donors for BMT, Bone Marrow Transplantation 11:37-41 (1993).
Dyer, P.A., et al, Matching for properdin factor B (Bf) in renal transplantation, Transplantation 32:424-425 (1981).
Fernando, et al., Assessment of Complement C4 Gene Copy Number Using the Paralog Ratio Test, Hum Mutat, 31(7):866-874 (2010).
Holzel, W.G.E., et al, Diagnostic validity of multivariate combinations of biochemical analytes as markers for rejection and infection in the follow-up of patients with heart transplants, J Clin Chem 26:667-671 (1988).
International Search Report issued in PCT/AU2014/000980 dated Nov. 28, 2014.
Metzker, Sequencing technologies—the next generation, Nat Rev Genet, 11(1):31-46 (2010).
Park, Y. et al., "Effect of major histocompatibility complex haplotype matching by C4 and MICA genotyping on acute graft versus host disease in unrelated hematopoietic stem cell transplantation", Human Immunology 77, 2016, 176-183.

(Continued)

*Primary Examiner* — Juliet C Switzer
(74) *Attorney, Agent, or Firm* — Knobbe, Martens, Olson & Bear LLP

(57) ABSTRACT

The present disclosure relates to the identification of single nucleotide polymorphisms (SNPs) in the Gamma genomic block in the central region of the major histocompatibility complex (MHC) that can be used for matching transplant donors and recipients and determining disease susceptibility.

19 Claims, 7 Drawing Sheets

Specification includes a Sequence Listing.

(56) References Cited

OTHER PUBLICATIONS

Petersdorf et al., MHC Haplotype Matching for Unrelated Hematopoietic Cell Transplantation, PLoS Med, 4(1):e8 (2007).
Petersdorf, et al., "MHC Haplotype Matching for Unrelated Hematopoietic Cell Transplantation", PLoS Med, 2007, 4:(1):e8.
Sato, T. et al., "Xeno-tissue typing (southern blot and xeno-MLR) in humans, monkeys, pics and beagles using HLA, SLA, C4A and Bf cDNA probes", Transplantation Proceedings 28, 1996, 1404-1405.
Sato, T. et al, Xeno-tissue typing (southern blot and xeno-MLR) in humans, monkeys, pics and beagles using HLA, SLA, C4A and Bf cDNA probes, Transplantation Proceedings 28:1404-1405 (1996).
Schneider, P. et al., "Complement C4 Protein and DNA Typing Methods", MCH Protocols, Methods in Molecular Biology vol. 210 Humana Press, 203, 269-295 (2003).
Shen et al., Multiplex target capture with double-stranded DNA probes, Genome Medicine, 5:50 (2013).
Yu, et al., Dancing with complement C4 and the RP-C4-CYP21-TNZ (RCCX) modules of the major histocompatibility complex, Progress in Nucleic Acid Research and Molecular Biology 75:217-292 (2003).
Candy, et al., Gama-type simple PCR-SSPS to enable the assessment of haplotype matching between unrelated stem cell donors and patients, Human Immunology, vol. 73:45 (2012).
Dawkins, et al., Genomics of the major histocompatibility complex: haplotypes, duplication, retroviruses and disease, Immunological Reviews, 167:275-304 (1999).
Kulsky, et al., Comparative genomic analysis of the MHC: the evolution of class I duplication blocks, diversity and complexity from shark to man, Immunological Reviews, 190:95-122 (2002).
The MHC sequencing consortium. Complete sequence and gene map of a human major histocompatibility complex, Nature 401:921-923 (1999).
Tochigi, et al., Association study between the TNXB locus and schizophrenia in a Japanese population, American Journal of Medical Genetics Part B (Neuropsychiatric Genetics), 144B:305-309 (2007).
Walsh, et al., An integrated haplotype map of the human major histocompatibility complex, Am. J. Hum. Genet., 73:580-590 (2003).
Morishima, et al., Impact of highly conserved HLA haplotype on acute graft-versus-host disease, Blood 115(23):4664-4670 (2010).

* cited by examiner

Figure 3

Matched

Mismatched

MAJOR HISTOCOMPATIBILITY COMPLEX SINGLE NUCLEOTIDE POLYMORPHISMS

RELATED APPLICATIONS

This application is a continuation of U.S. Ser. No. 15/029,224 filed Apr. 13, 2016 which is the U.S. National Phase of PCT Application No. PCT/AU2014/000980 filed Oct. 15, 2014 and published in English as WO/2015/054731 on Apr. 23, 2015 which claims priority to Australian Application No. 2013903971 filed on Oct. 15, 2013 which are each incorporated herein by reference in its entirety.

REFERENCE TO SEQUENCE LISTING

This application is being filed with a sequence listing in electronic format. The sequence listing is provided as a file entitled ILLINC338C1SEQLIST.TXT, created Mar. 21, 2019 which is approximately 10 kb in size. The information in the electronic format of the sequence listing is incorporated herein by reference in its entirety.

FIELD

The present disclosure relates to the identification of single nucleotide polymorphisms (SNPs) in the Gamma genomic block in the central region of the major histocompatibility complex (MHC) that can be used for matching transplant donors and recipients and determining disease susceptibility.

BACKGROUND

The Major Histocompatibility Complex (MHC) is a gene dense region of approximately 4 Mb on the short arm of chromosome 6. The MHC contains many immune response genes, including genes encoding the human leukocyte antigens (HLAs). The MHC also contains many genes involved in immunological and inflammatory responses and has been associated with numerous autoimmune and inflammatory disorders.

The MHC is usually inherited as a complete block; however, recombination has been shown to occur at frequencies of approximately 1/100 meioses at specific regions within the MHC. Between these recombination hot spots are genomic blocks of DNA up to several hundred kilobases in length. Thus, many unrelated individuals within a population either have a conserved haplotype, or recombined blocks from conserved haplotypes. The conserved haplotypes are referred to as "extended haplotypes" or "ancestral haplotypes".

There are 4 major genomic blocks within the MHC. The precise boundaries of these genomic blocks are unknown and smaller genomic blocks between the major genomic blocks are likely to exist. The major blocks are the alpha block, which includes HLA-A; the beta block, which includes HLA-B and HLA-C; the gamma block, which includes the Bf, C2 and C4 genes; and the delta block, which includes the HLA-DRB, and the DQB1 genes. The HLA-A, HLA-B, HLA-C, HLA-DRB1, HLA-DQB1 and HLA-DPB1 genes are presently used to match transplant donors and recipients. HLA-DPB1 is probably in a separate block centromeric of delta block due to the high rate of recombination seen between the genes of the delta block and HLA-DPB1. Nevertheless, HLA-DPB1 is frequently typed for transplantation matching. HLA matching has been shown to be critical for an improved outcome following stem cell transplantation. Furthermore, a study by Petersdorf et al. (2007) showed that the outcome following unrelated stem cell transplant was improved if HLA matched donors and recipients were haplotype-matched compared to donor/recipient pairs that were HLA-matched, but haplotype-mismatched. In this study, genomic DNA from both the donor and recipient was extracted and hybridized to microarrays containing oligonucleotide probes configured to detect physical linkage between the HLA alleles. This approach is not suitable to routine HLA typing and a routine test for assessing or improving the likelihood of haplotype matching has been, hitherto, undescribed.

In some aspects of molecular biology, a haplotype is described as the physical linkage that exists between 2 nucleotide polymorphisms. When referring to HLA and MHC, the term haplotype is used to describe the entire MHC, spanning at least HLA-A to HLA-DQB1. This region spans approximately 4 Mb and is usually inherited intact.

Some haplotypes remain intact for up to thousands of generations and remain identical in sequence except for a small number of SNPs between unrelated individuals. Different ancestral haplotypes contain unique combinations of HLA alleles and have unique sequence content in many regions throughout the MHC. It is likely that the haplotype/HLA matched individuals with reduced graft-versus-host disease (GVHD) compared with HLA matched but haplotype mismatched individuals is because haplotype matched individuals share a complete or partial ancestral haplotype and therefore also share many unique sequences.

The best stem cell donor is an identical twin, followed by an HLA haploidentical sibling. The relatively low probability of identifying an HLA haploidentical sibling often results in the need to identify suitable unrelated HLA-matched donors, which can be accessed through donor registries. However, despite being HLA-matched, the probability of a successful outcome is usually less than that of haploidentical siblings. It is thought that one reason for this disparity in outcome may be that haploidentical siblings are matched for other genes or sequences within the MHC that may contribute to transplantation outcome.

GVHD is a common complication following an allogeneic tissue transplant. It is commonly associated with stem cell or bone marrow transplant but the term also applies to other forms of tissue graft Immune cells (white blood cells) in the tissue (the graft) recognize the recipient (the host) as "foreign". The acute or fulminant form of the disease (aGVHD) is normally observed within the first 100 days post-transplant and is a major challenge to transplants owing to associated morbidity and mortality. Acute graft-versus-host-disease is characterized by selective damage to the liver, skin (rash), mucosa, and the gastrointestinal tract. Newer research indicates that other graft-versus-host-disease target organs include the immune system (the hematopoietic system, e.g., the bone marrow and the thymus) itself, and the lungs in the form of idiopathic pneumonitis.

Acute GVHD is staged and graded (0-IV) by the number and extent of organ involvement. Patients with grade IV GVHD usually have a poor prognosis. If the GVHD is severe and requires intense immunosuppression involving steroids and additional agents to get under control, the patient may develop severe infections as a result of the immunosuppression and may die of infection.

Accordingly, there remains a need for a testing method for identifying transplant donors for recipients such that the risk of the recipient developing aGVHD, and particularly stage IV (life threatening) aGVHD is reduced.

SUMMARY

The present inventors describe the identification of unique DNA sequence nucleotides or single nucleotide polymorphisms (SNPs) in coding and non-coding parts of the MHC gamma block, which is located between the HLA-B/C block (the delta block) and the HLA-DRB/DQB block (the delta block) of the MHC. A number of the identified SNPs are common to a number of ancestral haplotypes, while other identified SNPs are specific to an ancestral haplotype. When used together the SNPs provide a Gamma block SNP profile (GBSP). The inventors have shown that most unrelated, random individuals and therefore, individuals who are unlikely to be HLA matched, have unique or mismatched GBSPs and individuals who have identical GBSPs are likely to be HLA matched. Accordingly, these SNPs or GBSPs can be used to identify transplant donors for a recipient in need of a transplant. By matching MHC gamma block SNPs or GBSPs in both the potential transplant donor and the recipient, the transplant recipient's risk of developing GVHD in otherwise HLA mismatched donors is reduced. Furthermore when matching MHC the SNPs or GBSPs in both the unrelated potential transplant donor and the recipient when there is a single HLA type mismatch, the chances of survival after 5 years is much improved.

Thus, in a first aspect the present invention provides a method of identifying a transplant donor for a recipient in need of a transplant, the method comprising:
　a) determining the presence of one or more single nucleotide polymorphism alleles in the MHC gamma block of the recipient in need of a transplant;
　b) determining the presence of one or more single nucleotide polymorphism alleles in the MHC gamma block of one or more potential transplant donors; and
　c) identifying a transplant donor based on the presence of one or more single nucleotide polymorphism alleles in the MHC gamma block of both the transplant donor and the recipient in need of a transplant.

In one embodiment, the method comprises identifying a transplant donor based on the presence of at least 24 single nucleotide polymorphism alleles in the MHC gamma block of both the transplant donor and the recipient in need of a transplant.

In one embodiment, the single nucleotide polymorphisms are in the C4 gene.

In one particular embodiment, the single nucleotide polymorphism alleles are selected from C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170.

In a second aspect, the present invention provides a method of reducing the likelihood of a transplant recipient developing graft versus host disease, the method comprising:
　a) determining the presence of one or more single nucleotide polymorphism alleles in the MHC gamma block of a recipient in need of a transplant;
　b) determining the presence of one or more single nucleotide polymorphism alleles in the MHC gamma block of one or more potential transplant donors;
wherein the presence or absence of the one or more single nucleotide polymorphism alleles in the MHC gamma block of both the transplant recipient and the one or more potential transplant donors is indicative of a reduced likelihood of the transplant recipient developing graft versus host disease following transplantation of a graft from the transplant donor.

In one embodiment, the graft versus host disease is severe graft versus host disease.

In a third aspect, the present invention provides a method of increasing the duration of survival of a transplant recipient, the method comprising:
　a) determining the presence of one or more single nucleotide polymorphism alleles in the MHC gamma block of a recipient in need of a transplant;
　b) determining the presence of one or more single nucleotide polymorphism alleles in the MHC gamma block of one or more potential transplant donors;
wherein the presence or absence of the one or more single nucleotide polymorphism alleles in the MHC gamma block of both the transplant recipient and the one or more potential transplant donors is indicative that the transplant recipient will experience an increased duration of survival following a transplant of a tissue or organ from the transplant donor.

In one embodiment, the donor and recipient being matched at 9/10 HLA alleles and being matched for each of the MHC gamma block single nucleotide polymorphism alleles is indicative that the transplant recipient will experience an increased duration of survival following a transplant of a tissue or organ from the transplant donor.

The skilled person will appreciate that determining the presence or absence of one or more single nucleotide polymorphisms may comprise analysing one or more nucleic acid samples from the donor and/or recipient, or alternatively may involve obtaining predetermined information, such as nucleic acid sequence information or the read-out from a nucleic acid analysis, from another entity such as a pathology laboratory or genetic testing laboratory.

Thus, in one embodiment, determining the presence of one or more single polynucleotide polymorphism alleles in the MHC gamma block of the recipient in need of a transplant and/or the potential donor comprises obtaining predetermined MHC gamma block single nucleotide polymorphism allelic information and/or MHC gamma block haplotype information.

In another embodiment, determining the presence of one or more single nucleotide polymorphism alleles in the MHC gamma block of the recipient of the potential transplant donor comprises analysing a nucleic acid sample from the recipient and/or from the potential donor to determine the presence of the one or more single nucleotide polymorphism alleles.

Any suitable method known in the art may be used to determine the presence or absence of the one or more single nucleotide polymorphism alleles. For example, in one embodiment analysing the nucleic acid sample comprises performing a technique selected from one or more of PCR-SSP assay, allele-specific probe hybridization, allele-specific primer extension, allele-specific amplification, nucleic acid sequencing, 5' nuclease digestion, a molecular beacon assay, an oligonucleotide ligation assay, size analysis, single-stranded conformation polymorphism analysis, denaturing gradient gel electrophoresis and direct nucleotide sequencing.

In one embodiment, the method comprises obtaining a biological sample from the potential transplant donor and/or the recipient and isolating nucleic acid from the biological sample. In another embodiment, the nucleic acid sample is isolated from a biological sample obtained from the potential transplant donor and/or the recipient. The biological sample may be any suitable cells or tissue from which genomic DNA may be extracted, for example, the biological sample may be lymphocytes, whole blood, buccal swab, a biopsy, or frozen tissue.

The present inventors have found that matching the potential transplant donor and the recipient for multiple single nucleotide polymorphisms in the MHC gamma block further reduces the risk of the donor developing acute graft versus host disease. Thus, in one embodiment, the method comprises determining the presence of 2 or more single nucleotide polymorphism alleles in the MHC gamma block of both the potential transplant donor and the recipient. In a preferred embodiment, the methods of the invention comprise determining the presence of at least 25 single nucleotide polymorphism alleles in the MHC gamma block of both the potential transplant donor and the recipient.

In one embodiment, the one or more single nucleotide polymorphism alleles in the MHC gamma block is present in the C4 gene, wherein the C4 gene is a C4A gene or a C4B gene. Alternatively, the one or more single nucleotide polymorphism alleles is present in both a C4A gene and C4B gene.

In one particular embodiment, the one or more single nucleotide polymorphism alleles is selected from one or more of C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and/or A20170.

In another embodiment, the method comprises determining the presence of at least 24 of C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170.

The skilled person will appreciate that the method of the invention may be used in conjunction with the detection of one or more alleles in a gene or region other than the MHC gamma block, and/or in conjunction with the detection of an HLA haplotype. Thus, in one embodiment, the method of the invention further comprises detecting the presence of one or more other alleles or determining one or more other haplotypes in the recipient and the potential transplant donor.

In an embodiment, the method comprises determining one or more other HLA alleles and/or HLA haplotypes. In one particular embodiment, the method comprises determining one or more alleles or haplotypes of the HLA-A, HLA-B, HLA-C, HLA-DRB, HLA-DQB and/or HLA-DPB genes.

Accordingly, the method of the invention may comprise selecting a transplant donor based on:
i) the presence of one or more single nucleotide polymorphism alleles in the MHC gamma block of the potential transplant donor and the recipient, or
ii) the presence of one or more single nucleotide polymorphism alleles in the MHC gamma block and the presence of one or more other HLA alleles and/or HLA haplotypes in the potential transplant donor.

In a fourth aspect, the present invention provides a method of transplanting an allogeneic graft into a recipient, the method comprising:
i) selecting a transplant donor according to the method of the invention,
ii) removing a donor graft from the transplant donor, and
iii) transplanting the graft into the recipient.

In one embodiment, the graft is an allogeneic stem cell transplant.

In one particular embodiment, the stem cell transplant is a hematopoietic stem cell transplant.

In a fifth aspect, the present invention provides a kit for matching a transplant donor and a recipient, the kit comprising:
a) a nucleic acid reagent for detecting one or more single nucleotide polymorphism alleles in the MHC gamma block; and
b) instructions for detecting the one or more single polynucleotide polymorphism alleles.

In one embodiment, the nucleic acid reagent for detecting one or more single nucleotide polymorphism alleles may be one or more oligonucleotide probes, such as oligonucleotide probes specific for one or more single nucleotide polymorphism alleles in the MHC gamma block. In one particular embodiment, the oligonucleotide probes are specific for one or more single nucleotide polymorphism alleles in the C4 gene.

In another embodiment, the oligonucleotide probes are detectably labelled.

In one embodiment, the oligonucleotide probes are specific for one or more single polynucleotide alleles selected from C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and/or A20170.

In another embodiment, the kit comprises oligonucleotide probes specific for each of C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170.

In yet another embodiment, the kit comprises oligonucleotide primers for amplifying one or more single nucleotide polymorphism alleles in the MHC gamma block. The oligonucleotide primers may be, for example, allele specific PCR amplification primers.

In one embodiment, the oligonucleotide primers are for amplifying one or more single nucleotide polymorphism alleles in the C4 gene.

In one embodiment, the kit comprising oligonucleotide primers further comprises DNA polymerase.

In one embodiment, the kit is suitable for performing one or more PCR-SSP assays.

In yet another embodiment, the kit comprises a multi-well plate.

In yet another embodiment, the kit comprises a negative amplification control.

In one embodiment, the kit comprises oligonucleotide primers for amplifying one or more single nucleotide polymorphism alleles selected from C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and/or A20170.

In another embodiment, the kit comprises oligonucleotide primers for amplifying each of C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170.

In one particular embodiment, the kit comprises one or more oligonucleotide primers comprising a sequence selected from any one or more of SEQ ID Nos:3 to 50.

The present invention further provides a nucleotide array for matching a transplant donor and a recipient, the nucleotide array comprising probes specific for one or more single nucleotide polymorphism alleles in the MHC gamma block.

In one embodiment, the probes are specific for one or more single nucleotide polymorphism alleles in the C4 gene.

In another embodiment, the kit comprises probes specific for at least 24 single nucleotide polymorphism alleles.

In one particular embodiment, the kit comprises probes specific for at least 24 single nucleotide polymorphism alleles in the C4 gene. In one embodiment, the kit comprises probes specific for each of C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170.

In a sixth aspect, the present invention provides a method of performing one or more PCR-SSP assays to detect single nucleotide polymorphisms in the MHC gamma block, the method comprising:
  i) mixing genomic DNA with a DNA polymerase to form a DNA-polymerase mix,
  ii) forming a reaction mixture by combining the DNA-polymerase mix with oligonucleotide primers for amplifying a single nucleotide polymorphism allele from the MHC gamma block,
  iii) subjecting the reaction mixture to thermal cycling to produce an amplification product, and
  iv) analysing the amplification product to detect the single nucleotide polymorphism.

In one particular embodiment, the amplification product is analysed by agarose gel electrophoresis.

In one embodiment, the genomic DNA is high molecular weight human genomic DNA.

In yet another embodiment, the genomic DNA is at a concentration of about 20 ng/μl to about 100 ng/μl.

In one embodiment, the method comprises extracting the genomic DNA from a biological sample.

In one particular embodiment, the method comprises extracting the genomic DNA from acid-citrate-dextrose solution (ACD) or EDTA anti-coagulated whole blood.

In yet another embodiment, the genomic DNA has an optical density (OD) ratio measurement of $OD_{260/280}>1.8$.

The single nucleotide polymorphism allele may be located anywhere in the MHC gamma block. In one embodiment, the single nucleotide polymorphism allele is in the C4 gene.

In one embodiment, the single nucleotide allele polymorphism is selected from C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and/or A20170.

In another embodiment, the method comprises detecting at least 24 single nucleotide polymorphism alleles.

In a seventh aspect, the present invention provides a method of identifying a transplant donor for a recipient in need of a transplant, the method comprising performing the method of performing one or more PCR-SSP assays of the invention to identify single nucleotide polymorphisms in the MHC gamma block of a transplant recipient and/or potential transplant donor.

In one embodiment of the first, third, fourth or seventh aspects of the invention, the donor and recipient are matched at 9/10 HLA alleles and are matched for each of the MHC gamma block single nucleotide polymorphism alleles.

In an eighth aspect, the present invention provides a method of reducing the likelihood of a transplant recipient developing graft versus host disease, the method comprising performing the method of performing one or more PCR-SSP assays of the invention to identify single nucleotide polymorphisms in the MHC gamma block of a transplant recipient and/or potential transplant donor.

In an ninth aspect, the present invention provides use of the kit of the invention, or the nucleotide array of the invention, for identifying single nucleotide polymorphisms in the MHC gamma block of a transplant recipient and/or potential transplant donor.

In one embodiment of the first to fifth and seventh to ninth aspects, the recipient in need of a transplant, or transplant recipient, is in need of or receives a hematopoietic stem cell transplant.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

| | | |
|---|---|---|
| 1: HLA-A*01:01; 24:02; | B*08:01; | DRB1*03:01, DQB1*02:01 |
| 2: HLA-A*02:01, | B*46:01, | DRB1*08:01 DQB1*06 |
| 3: HLA-A*30:02; 68:01, | B*42:01, | DRB1*03:02 DQB1*04 |
| 4: HLA-A*24:02, | B*52:01, | DRB1*15:01, DQB1*06:02 |

Figure 3:
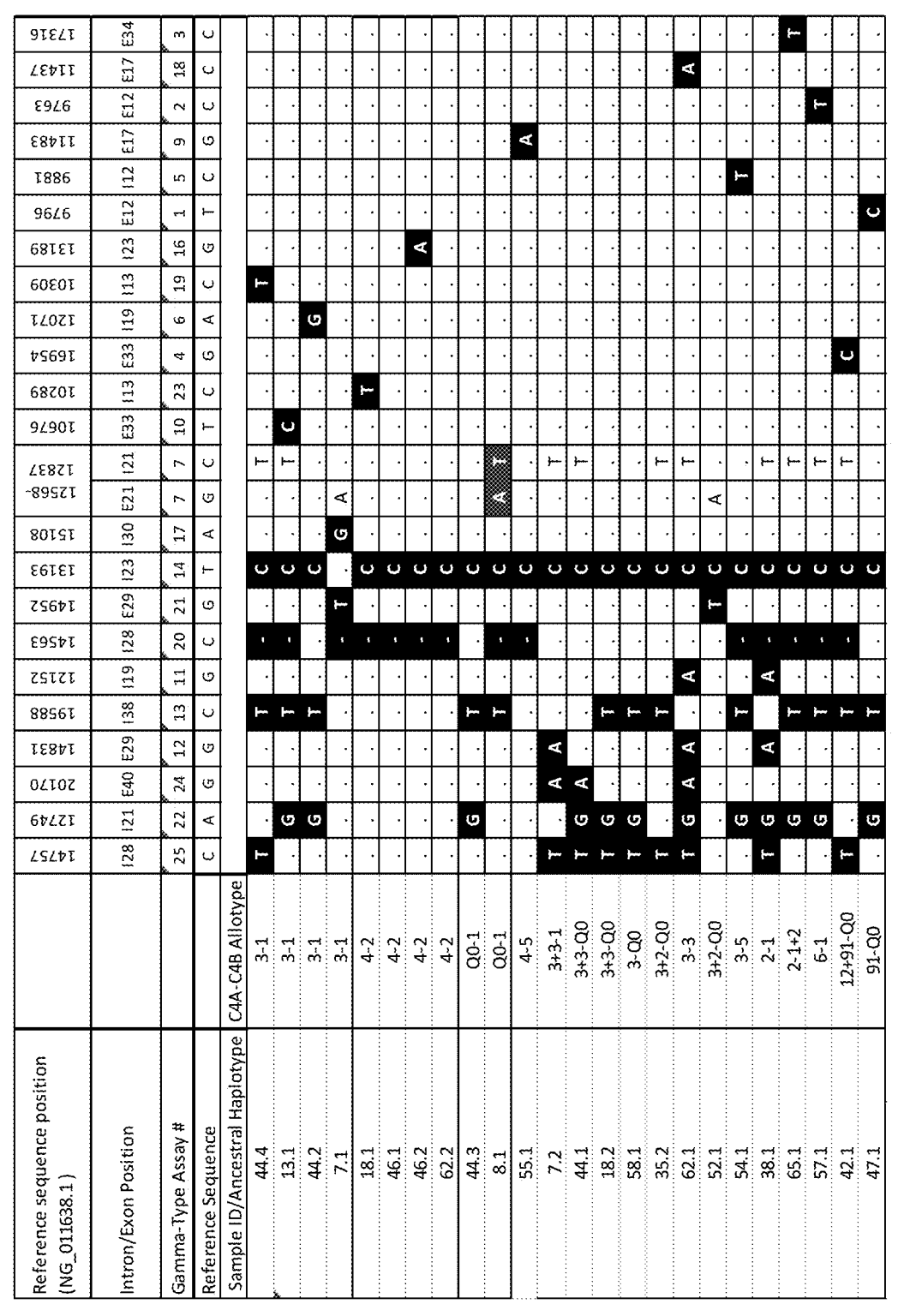

FIG. 3. Table of SNPs identified on the different samples tested compared to the reference sequence. The sequences in the black boxes are the SNPs detected by the Gamma-Type assay. The sequence differences that are in black text and white boxes are sequence differences compared with the reference but are not uniquely targeted by the Gamma-Type assay. The Gamma-Type assay #7 requires the presence of 2×SNPs that need to be present in linkage with each other. A black box with a white dash (-) indicates a deletion relative to the reference. The samples are labelled according to their ancestral haplotype and the C4 allotype of the samples is shown.

Figure 4:
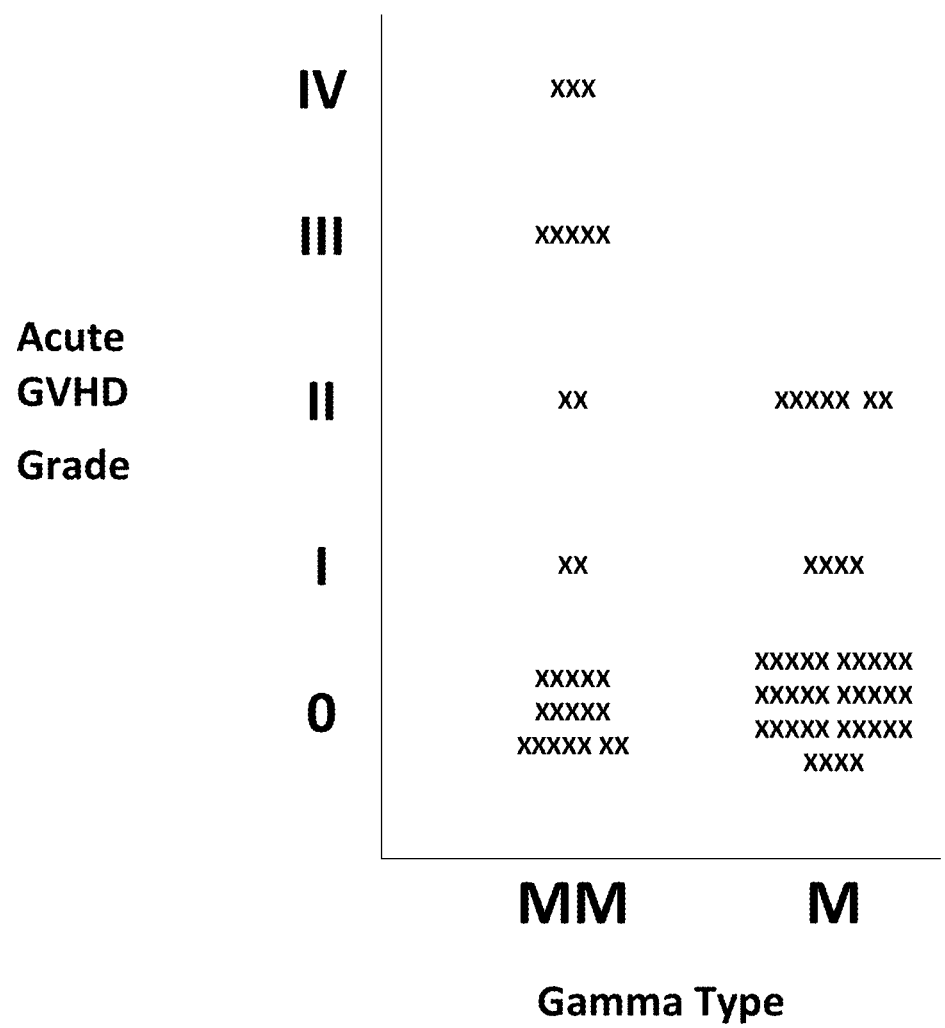

FIG. 4. Gamma-Type Mismatching results in an increased risk of severe aGVHD. Patients (x) matched (M) and mismatched (MM) for Gamma-Type and whether the patient was diagnosed with Acute GVHD and Acute GVHD grade.

Figure 5:
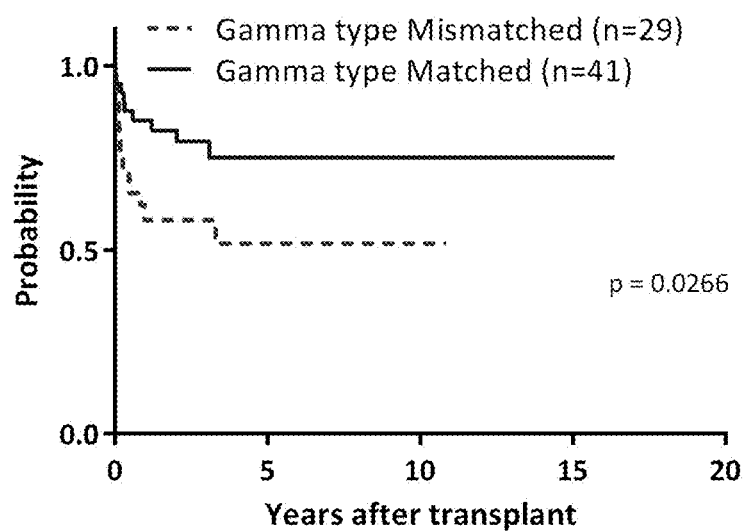

FIG. 5. Gamma-Type Matching results in improved chances of long-term survival.

Figure 6:
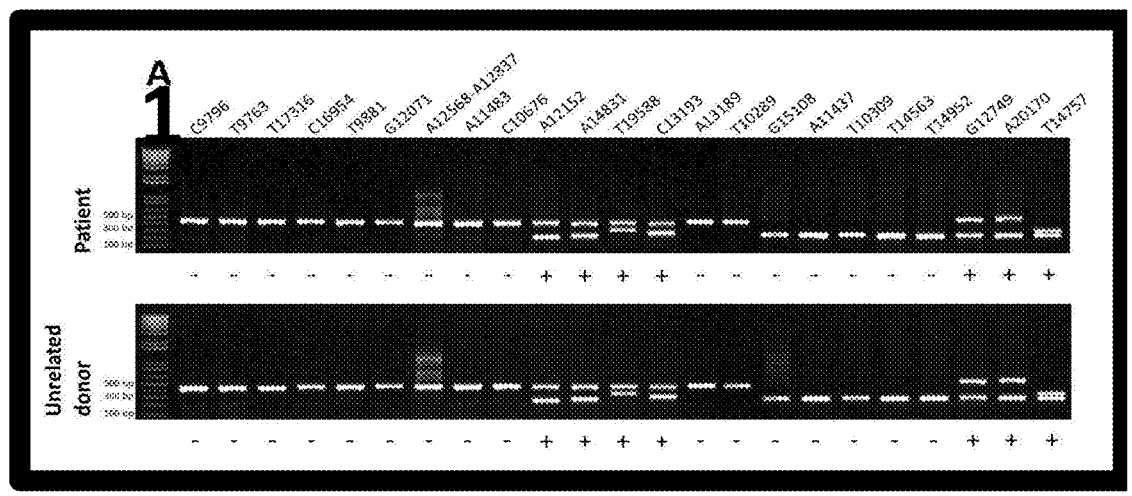
Figure 6:
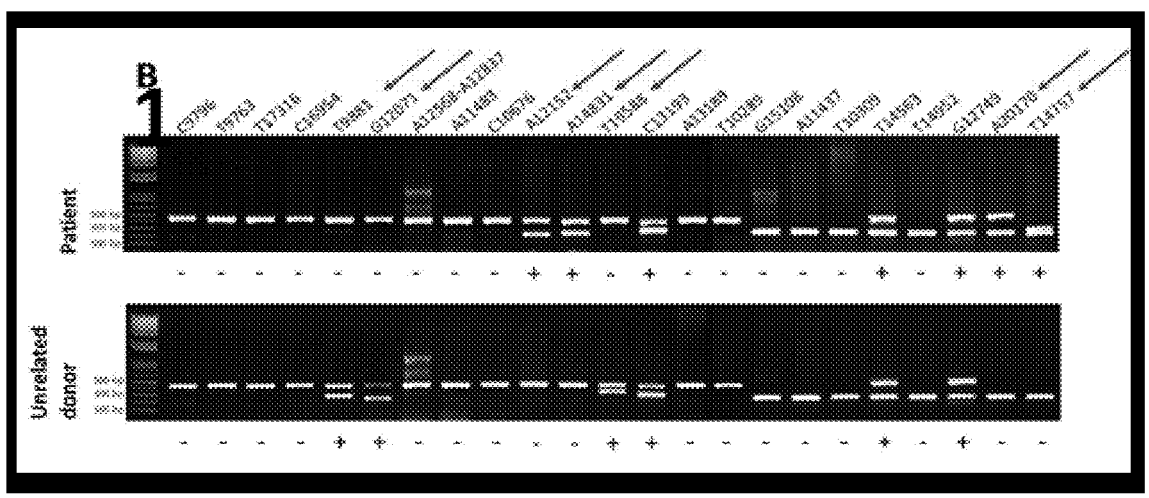

FIG. 6. Gamma-Type PCR SSP analysis for both Gamma-Type matched (A) and mismatched (B) individuals in unrelated donors and patients. Arrows indicate mismatched SNP alleles.

Figure 7:
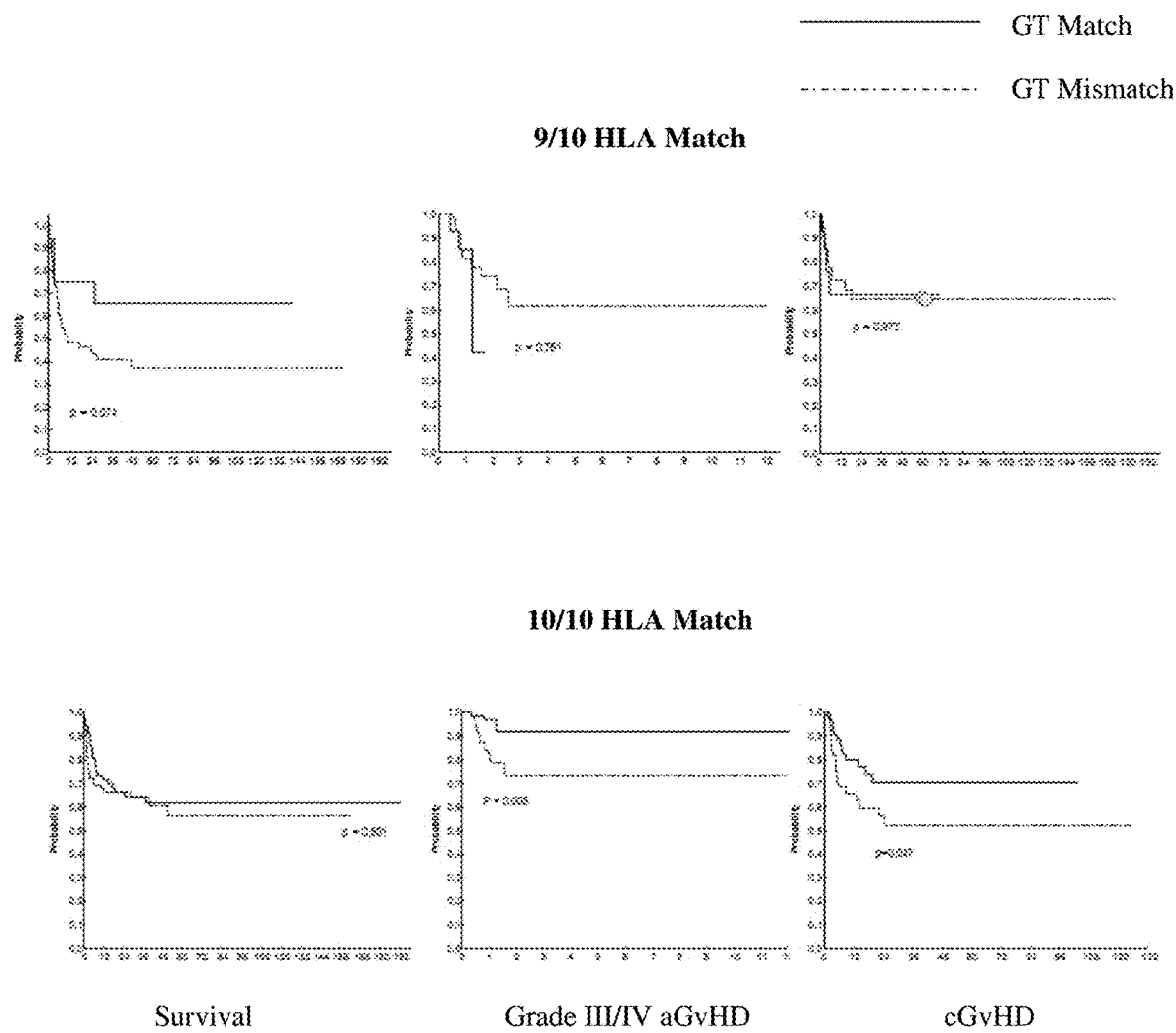

FIG. 7. Results of the retrospective study showing differences in survival, grade III/IV aGvHD, and cGvHD in GT matched and GT mismatched unrelated patient donor pairs.

KEY TO THE SEQUENCE LISTING

SEQ ID NO:1—C4A isotype-specific amino acid residues.

SEQ ID NO:2—C4B isotype-specific amino acid residues.

SEQ ID NOs:3-50—oligonucleotide primers.

DETAILED DESCRIPTION

General Techniques and Definitions

Unless specifically defined otherwise, all technical and scientific terms used herein shall be taken to have the same meaning as commonly understood by one of ordinary skill in the art (e.g., in molecular genetics, biochemistry, and immunology).

Unless otherwise indicated, the molecular genetics, biochemistry, and immunological techniques utilized in the present invention are standard procedures, well known to those skilled in the art. Such techniques are described and explained throughout the literature in sources such as, J, Perbal, A Practical Guide to Molecular Cloning, John Wiley and Sons (1984), J. Sambrook and Russell., Molecular Cloning: A Laboratory Manual, $3^{rd}$ edn, Cold Spring Harbour Laboratory Press (2001), R. Scopes, Protein Purification-Principals and Practice, 3' edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "nucleic acid" or "nucleic acid sequence" or "nucleic acid molecule" refers to deoxyribonucleotides or ribonucleotides and polymers thereof in either single- or double-stranded form. The term nucleic acid is used interchangeably with gene, complementary DNA (cDNA), messenger RNA (mRNA), oligonucleotide, and polynucleotide.

By "isolated nucleic acid molecule" we mean a nucleic acid molecule which has generally been separated from the nucleotide sequences with which it is associated or linked in its native state (if it exists at all in nature). Preferably, the isolated nucleic acid is at least 60% free, more preferably at least 75% free, and more preferably at least 90% free from other components with which it is normally associated. The nucleic acid may be isolated from a biological sample using any suitable known technique. For example, total genomic DNA may be extracted from cells using methods known in the art and/or commercially available kits, e.g., by using the QIAamp DNA blood Mini Kit or the DNeasy Blood & Tissue Kit supplied by QIAGEN, or by using methods such as phenol/chloroform extraction and ethanol precipitation.

The term "probe" according to the present invention refers to a single-stranded oligonucleotide which is designed to specifically hybridize to a nucleic acid comprising a C4 gene single nucleotide polymorphism. The probes of the invention may be about 5 to 150 nucleotides long. In one embodiment, the probe may be used in high-throughput (next-gen) sequencing using a target capture technique. Thus, in one embodiment, the probe may be suitable for target capture and be around 60 to 120 nucleotides in length.

Alternatively, the probe may be about 10 to 25 nucleotides. In certain embodiments, the length of the probe is 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups which do not essentially alter their hybridization characteristics.

The "biological sample" may be for instance lymphocytes, whole blood, buccal swab, biopsy sample or frozen tissue or any other sample comprising genomic DNA. Although almost any tissue source can be used for molecular genotyping, lymphocytes from peripheral blood, for example, are most often used. It is also possible to utilise samples obtained through non-invasive means, for example by way of cheek swab or saliva-based DNA collection. Various suitable methods for extracting DNA from such sources are known in the art. These range from organic solvent extraction to absorption onto silica coated beads and anion exchange columns Automated systems for DNA extraction are also available commercially and may provide good quality, high purity DNA.

As used herein, the terms "transplant" or "transplanting" refer to the grafting or introduction of tissue or cells obtained from one individual (the donor) into or onto the body of another individual (the recipient). The cells or tissue that are removed from the donor and transplanted into the recipient are referred to as a "graft". Examples of tissues commonly transplanted are bone marrow, hematopoietic stem cells, organs such as liver, heart, skin, bladder, lung, kidney, cornea, pancreas, pancreatic islets, brain tissue, bone, and intestine. In one embodiment, the transplant is a hematopoietic stem cell transplant.

The person skilled in the art would understand that the term "haplotype" refers to a combination of alleles that are located closely, or at adjacent loci, on a chromosome and that are inherited together, or a set of single nucleotide polymorphisms on a single chromosome of a chromosome pair that are statistically associated.

MHC Gamma Block

Figure 1:
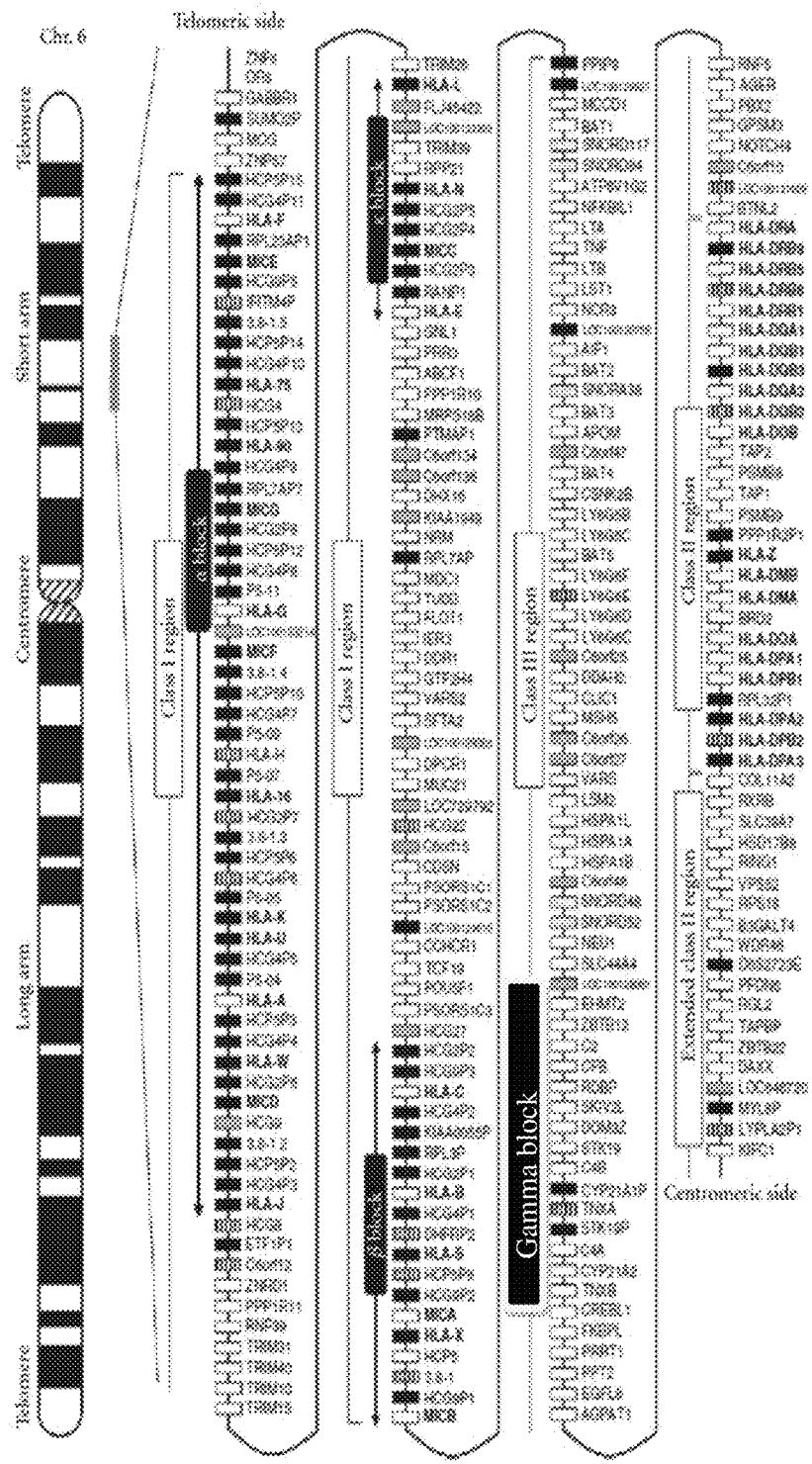
FIG. 1. Diagram showing the location of the MHC gamma block region on chromosome 6.

As used herein the term "MHC gamma block" refers to the genomic region which is located between the HLA-B/C block (the delta block) and the HLA-DRB/DQB block (the delta block) of the major histocompatibility complex (MHC) on the short arm of chromosome 6 (FIG. 1). Genes located in the MHC gamma block include, but are not limited to, TNXB (OMIM 600985), CYP21A2 (OMIM 613815), C4A (OMIM 120810), STK19 (OMIM 604977), C4B (OMIM 120820), DOM3Z (OMIM 605996), SKIVL2 (OMIM 600478), RDBP (OMIM 154040), CFB (OMIM 138470), C2 (OMIM 613927), and EHMT2 (OMIM 604599).

The human complement C4 locus is in the class III region of the MHC and exhibits genetic complexity. Complement C4 genes show segmental duplication as part of mono-, bi-, tri-, or quadrimodular RCCX cassettes (Fernando et al., 2010). Hence, in theory, two to eight copies of C4 genes may be present in a diploid human genome; with each chromosome 6 comprising one to four copies of a single C4 gene. The C4 gene exists as either of two forms: C4A (acidic) (OMIM reference: 120810) or C4B (basic) (OMIM reference: 120820), each of which is polymorphic in itself. As used herein, the term "C4 gene" refers to a polynucleotide sequence that may be either a C4A or C4B gene form.

At the nucleotide level C4A and C4B share 99% sequence homology over 41 exons. Each isotype is defined by five nucleotide changes in exon 26, which contribute to four isotype-specific amino acid residues from 1120 to 1125: PCPVLD (SEQ ID NO:1) for C4A and LSPVIH (SEQ ID NO:2) for C4B. The C4A and C4B proteins differ in chemical reactivity. C4A preferentially binds to amino groups, forming amide bonds with proteins such as immune complexes. C4B demonstrates greater haemolytic activity in certain immunoassays compared to C4A and has a higher affinity for hydroxyl groups. C4 genes may also vary in size, occurring as long (C4L) or short (C4S) forms. The long (21 kb) or short (14.6 kb) forms of the C4 gene are determined by the presence or absence of a 6.4 kb insertion of human endogenous retrovirus, HERV-K(C4), into intron 9.

The method of the present invention described herein relates to determining a likelihood of development of aGVHD and/or duration of transplant patient survival in a patient by matching single nucleotide polymorphism alleles in the MHC gamma block of one or more potential transplant donors with one or more single nucleotide polymorphism alleles in the MHC gamma block in a recipient in need of a transplant. Thus, the method of the invention finds use in a variety of applications. For example, the method of the invention may be used to identify a candidate donor for a transplant recipient, wherein a graft from the donor would be less likely to result in aGVHD, particularly severe aGHVD, in the recipient when compared to a transplant donor with fewer single nucleotide polymorphism alleles matching those of the recipient.

The present inventors have found that matching one single nucleotide polymorphism allele in the MHC gamma block of both the transplant donor and the recipient reduces the risk of the recipient developing severe acute graft versus host disease. Thus, in one embodiment, the method comprises determining the presence of one single nucleotide polymorphism allele in both the potential transplant donor and the recipient. The present inventors have also found that matching the potential transplant donor and the recipient for additional single nucleotide polymorphism alleles in the MHC gamma block further reduces the risk of the donor developing acute graft versus host disease, and particularly severe acute graft versus host disease. Thus, in one embodiment, the method comprises determining the presence of 2 or more, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more single nucleotide polymorphism alleles in the MHC gamma block of both the potential transplant donor and the recipient. In one particular embodiment, the method comprises determining the presence of 24 or 25 single nucleotide polymorphism alleles in both the potential transplant donor and the recipient.

In one embodiment, the methods of the invention comprise determining the presence of one or more SNP alleles in the coding or non-coding regions of at least one MHC gamma block gene selected from TNXB, CYP21A2, C4A, STK19, C4B, DOM3Z (OMIM 605996), SKIVL2, RDBP, CFB, C2, and EHMT2.

In one embodiment, the methods of the invention comprise determining the presence of one or more SNP alleles in the C4 gene selected from C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170. The skilled person will understand that the locations of these SNP alleles are relative to the first base of the initiation codon of the C4 gene.

In one particular embodiment, the methods of the invention comprise determining the presence of each of at least 24 SNP alleles selected from the C2321, T9763, C9796, T9819, T9881, T10289, T10309, C10676, A11437, A11483, G12071, A12152, A12568, A12837, G12749, A12877, A13189, C13193, A13950, A14483, T14563, T14757, A14831, T14952, G15108, C16954, T17316, T19588, and A20170 SNP alleles. In another embodiment, the methods of the invention comprise detecting one or more further SNPs in the C4 gene.

In addition, determination of a likelihood of developing aGVHD in a transplant candidate may influence the determination as to whether transplantation is indeed the most suitable form of treatment for their condition. In some instances, there may be alternate forms of therapy available which would provide a better prognosis to the patient. Also, prediction of a likelihood of aGVHD would be indicative of the necessity for treatment regimes, or possibly more aggressive treatment regimens than would otherwise be recommended. Such aggressive therapies often have undesirable side effects and so preferably are not used unless prognosis indicates a need. For example, treatment of patients with neutralizing anti-TNF-alpha monoclonal antibodies can result in amelioration of aGVHD, but can increase risk of infections. Various aggressive anti-inflammatory therapies are also available.

Single Nucleotide Polymorphisms (SNPs)

The genomes of all organisms undergo spontaneous mutation in the course of their continuing evolution, generating variant forms of progenitor genetic sequences. The coexistence of multiple forms of a genetic sequence gives rise to genetic polymorphisms, including single nucleotide polymorphisms, otherwise known as "SNPs". SNPs can also arise in areas of the genome with no apparent function, but the SNP can be genetically linked to a variant sequence in the genome. Thus, the SNP can closely correlate with the variant sequence of the genome, depending on how close the genetic linkage is.

SNPs are single base positions in DNA at which different alleles, or alternative nucleotides, exist in a population. For example, two sequenced DNA fragments from different individuals, AAGCCTA to AAGCTTA, contain a difference in a single nucleotide. In this case we say that there are two alleles. Most common SNPs have only two alleles.

Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand to refer to a particular SNP position, SNP allele, or nucleotide sequence. The position of a SNP may also be determined by reference to the first base of the initiation codon (also referred to as the "start" codon) of the gene.

Detection of Single Nucleotide Polymorphisms

Any suitable technique known in the art that allows for the qualitative and/or quantitative assessment of single nucleotide polymorphism alleles in a sample may be used. In addition, comparison may be made by reference to a standard control or control sample.

Methods that may be used for the detection of single nucleotide polymorphisms include PCR, LCR (ligand chain reaction) and hybridization techniques. The "polymerase chain reaction" ("PCR") is a reaction in which replicate copies are made of a target polynucleotide using a "pair of primers" or "set of primers" consisting of a "forward" and a "reverse" primer, and a catalyst of polymerization, such as a DNA polymerase, and typically a thermally-stable polymerase enzyme. Methods for PCR are known in the art, and are taught, for example, in "PCR" (Ed. M J. McPherson and S. G Moller (2000) BIOS Scientific Publishers Ltd, Oxford). PCR can be performed on cDNA obtained from reverse transcribing mRNA isolated from biological samples.

A primer is often an oligonucleotide, generally of about 20 nucleotides long, with a minimum of about 15 nucleotides in length, which is capable of hybridising in a sequence specific fashion to the target sequence and being extended during the PCR. Longer nucleic acid molecules, for example nucleic acid molecules at least 50 or 100 or more nucleotides in length may also be used as a primer Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may also contain additional sequences and/or modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Another nucleic acid amplification technique is reverse transcription polymerase chain reaction (RT-PCR). First, complementary DNA (cDNA) is made from an RNA template, using a reverse transcriptase enzyme, and then PCR is performed on the resultant cDNA.

Another method for amplification is the ligase chain reaction ("LCR"), disclosed in EP 0 320 308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Other methods for amplification of nucleic acid molecules are known to those skilled in the art and include isothermal amplification methods and transcription-based amplification systems. Any suitable method for amplifying a nucleic acid construct, or fragment thereof, or an isolated or exogenous nucleic acid molecule, or a fragment thereof, may be used in the methods of the present invention.

Allele specific PCR (such as ASA, ARMS, SSP) is a useful technique in genotyping as it allows the detection of polymorphisms in a cis-located method. The method has been popularised as a rapid and relatively easy method of genotyping by numerous applications particularly in the field of HLA genotyping and other complex genotyping applications such as ABO genotyping.

Genotyping method, kits and compositions of the present invention may comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or greater primers or forward/reverse primer pairs. Particularly such primers are for amplifying one or more single nucleotide polymorphism allele loci in the C4 gene.

Hybridization techniques involve detecting the hybridization of two or more nucleic acid molecules, where detection is achieved in a variety of ways, including labeling the nucleic acid molecules and observing the signal generated from such a label. Hybridization techniques may include any of the following: Northern and Southern blotting, cycling probe reaction, branched DNA, Invader Assay, and Hybrid Capture. Hybridization techniques may also be used to identify a specific sequence of nucleic acid present in a sample by using microarrays of known nucleic acid sequences to probe a sample. Array technologies may use known single stranded nucleic acid, where each unique short chain is attached in a specific known location and then adding the sample nucleic acid and allowing sequences present in the sample to hybridize to the immobilized strands. Detection of this hybridization is then carried out by labeling, such as end labeling, of the fragments of the sample to be detected prior to the hybridization. Further, hybridization may be determined by use of a fluorescent in situ hybridization technique.

Common genotyping methods that can be utilized in the method of the present invention include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, oligonucleotide ligation assay (OLA), multiplex ligation reaction sorted on genetic arrays, restriction-fragment length polymorphism, single base extension-tag assays, and the Invader assay. Such methods may be used in combination with detection mechanisms such as, for example, luminescence or chemi-luminescence detection, fluorescence detection, time-resolved fluorescence detection, fluorescence resonance energy transfer, fluorescence polarization, mass spectrometry, and electrical detection.

Other methods for detecting polymorphisms include, but are not limited to, methods in which protection from cleavage agents is used to detect mismatched bases in RNA/RNA or RNA/DNA, comparison of the electrophoretic mobility of nucleic acid molecules, and assaying the movement of polymorphic fragments in polyacrylamide gels containing a gradient of denaturant using denaturing gradient gel electrophoresis. Sequence variations at specific locations can also be assessed by nuclease protection assays such as RNase and SI protection or chemical cleavage methods.

In one embodiment, detection of one or more SNPs or haplotyping is performed using the TaqMan assay, which is also known as the 5' nuclease assay. The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target SNP-containing template which is amplified during PCR, and the probe is designed to hybridize to the target SNP site only if a particular SNP allele is present.

Preferred TaqMan primer and probe sequences can readily be determined using the SNP and associated nucleic acid sequence information as described herein. A number of computer programs, such as Primer Express (Applied Biosystems, Foster City, Calif.), can be used to rapidly obtain optimal primer/probe sets. It will be apparent to one of skill in the art that such primers and probes for detecting the SNP alleles are useful in the methods of the invention, and can be readily incorporated into a kit format.

In the oligonucleotide ligation assay (OLA), one probe hybridizes to a segment of a target nucleic acid with its 3' most end aligned with the nucleic acid site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the nucleic acid site. If there is a mismatch, efficient ligation cannot occur. After the reaction, the ligated probes are separated from the target nucleic acid molecule, and detected as indicators of the presence of a nucleic acid sequence. OLA may also be used for performing nucleic acid detection using universal arrays, wherein a zipcode sequence can be introduced into one of the hybridization probes, and the resulting product, or amplified product, hybridized to a universal zip code array. Alternatively OLA may be used where zipcodes are incorporated into OLA probes, and amplified PCR products are determined by electrophoretic or universal zipcode array readout.

Alternatively one may use SNPlex methods and software for multiplexed SNP detection using OLA followed by PCR, wherein zipcodes are incorporated into OLA probes, and amplified PCR products are hybridized with a zipchute reagent, and the identity of the SNP determined from electrophoretic readout of the zipchute. In some embodiments, OLA is carried out prior to PCR (or another method of nucleic acid amplification). In other embodiments, PCR (or another method of nucleic acid amplification) is carried out prior to OLA.

Another method for determining SNPs and SNP haplotypes is based on mass spectrometry. Mass spectrometry takes advantage of the unique mass of each of the four nucleotides of DNA. Nucleic acids can be unambiguously genotyped by mass spectrometry by measuring the differences in the mass of nucleic acids having alternative nucleic acid alleles. MALDI-TOF (Matrix Assisted Laser Desorption Ionization-Time of Flight) mass spectrometry technology is preferred for extremely precise determinations of molecular mass, such as for SNPs. Numerous approaches to genotype analysis have been developed based on mass spectrometry. Preferred mass spectrometry-based methods of nucleic acid genotyping include primer extension assays, which can also be utilized in combination with other approaches, such as traditional gel-based formats and microarrays.

Typically, the primer extension assay involves designing and annealing a primer to a template PCR amplicon upstream (5') from a target nucleic acid position. A mix of dideoxynucleotide triphosphates (ddNTPs) and/or deoxynucleotide triphosphates (dNTPs) are added to a reaction mixture containing template. For example, in some embodiments this is a SNP-containing nucleic acid molecule which has typically been amplified, such as by PCR. Primer and DNA polymerase may further be added. Extension of the primer terminates at the first position in the template where a nucleotide complementary to one of the ddNTPs in the mix occurs. The primer can be either immediately adjacent (i.e., the nucleotide at the 3' end of the primer hybridizes to the nucleotide next to the target SNP site) or two or more nucleotides removed from the nucleic acid position. If the primer is several nucleotides removed from the target nucleic acid position, the only limitation is that the template sequence between the 3' end of the primer and the nucleic acid position cannot contain a nucleotide of the same type as the one to be detected, or this will cause premature termination of the extension primer.

Alternatively, if all four ddNTPs alone, with no dNTPs, are added to the reaction mixture, the primer will always be extended by only one nucleotide, corresponding to the target SNP position. In this instance, primers are designed to bind one nucleotide upstream from the SNP position (i.e., the nucleotide at the 3' end of the primer hybridizes to the nucleotide that is immediately adjacent to the target SNP site on the 5' side of the target SNP site). Extension by only one nucleotide is preferable, as it minimizes the overall mass of the extended primer, thereby increasing the resolution of mass differences between alternative SNP nucleotides. Furthermore, mass-tagged ddNTPs can be employed in the primer extension reactions in place of unmodified ddNTPs. This increases the mass difference between primers extended with these ddNTPs, thereby providing increased sensitivity and accuracy, and is particularly useful for typing heterozygous base positions. Mass-tagging also alleviates the need for intensive sample-preparation procedures and decreases the necessary resolving power of the mass spectrometer.

The extended primers can then be purified and analyzed by MALDI-TOF mass spectrometry to determine the identity of the nucleotide present at the target SNP position. In one method of analysis, the products from the primer extension reaction are combined with light absorbing crystals that form a matrix. The matrix is then hit with an energy source such as a laser to ionize and desorb the nucleic acid molecules into the gas-phase. The ionized molecules are then ejected into a flight tube and accelerated down the tube towards a detector. The time between the ionization event, such as a laser pulse, and collision of the molecule with the detector is the time of flight of that molecule. The time of flight is precisely correlated with the mass-to-charge ratio (m/z) of the ionized molecule. Ions with smaller m/z travel down the tube faster than ions with larger m/z and therefore the lighter ions reach the detector before the heavier ions. The time-of-flight is then converted into a corresponding, and highly precise, m/z. In this manner, SNPs can be identified based on the slight differences in mass, and the corresponding time of flight differences, inherent in nucleic acid molecules having different nucleotides at a single base position.

Nucleic acids can also be scored by direct DNA sequencing. A variety of automated sequencing procedures can be used, including sequencing by mass spectrometry. In light of the teachings herein, one of ordinary skill in the art can readily design sequencing primers for such automated sequencing procedures. Commercial instrumentation, such as the Applied Biosystems 377, 3100, 3700, 3730, and 3730×1 DNA Analyzers (Foster City, Calif.), is commonly used in the art for automated sequencing. Nucleic acid sequences can also be determined by employing a high throughput mutation screening system, such as the Spectru Medixsystem.

In one embodiment, the presence of the one or more single nucleotide polymorphism alleles is determined using a Next-generation sequencing (NGC) technology. Next-generation sequencing (NGS) technologies include instruments that are capable of sequencing more than 1014 kilobase-pairs (kbp) of DNA per instrument run. Sequencing typically produces a large number of independent reads, each representing anywhere between 10 to 1000 bases of the nucleic acid. Nucleic acids are generally sequenced redundantly for confidence, with replicates per unit area being referred to as the coverage (i.e., "10× coverage" or "100× coverage"). Next generation sequencing methods are known in the art, and are described, for example, in Metzker (2010).

Thus, the terms "Next-generation sequencing" or "NGS" or "NG sequencing" as used herein refer to any sequencing method that determines the nucleotide sequence of either individual nucleic acid molecules (e.g., in single molecule sequencing) or clonally expanded proxies for individual nucleic acid molecules in a high through-put fashion (e.g., greater than 103, 104, 105 or more molecules are sequenced simultaneously).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

In one embodiment, determining the presence of one or more SNPs involves targeted next generation sequencing (also referred to as "target capture" or "sequence capture" next generation sequencing). Such target enrichment technologies utilize single-stranded oligonucleotide probes to capture candidate genomic regions from a DNA sample before sequencing (see, for example, Shen et al., 2013). There are now several target enrichment strategies with the common goal to capture candidate genomic regions at high accuracy and completeness, while lowering the costs at the same time. The most widely used methods utilize multiplex PCR amplification, hybrid-capture, selective target circularization, and oligonucleotide-selective sequencing.

HLA Alleles and HLA Typing

The skilled person will appreciate that the method of the present invention may be used in conjunction with HLA-typing. The term "typing" when used in relation to an HLA-allele refers to identification of an allele, i.e. detection of the allele and discrimination of the allele from other alleles of the same locus. Thus, the methods of the invention may further involve determining the presence of one or more HLA SNPs in a gene other than C4, or determining an HLA haplotype for one or more genes other than the C4 gene in the potential transplant donor and/or the recipient. As used herein, the term "haplotype" refers to any combination of genetic variants or markers ("alleles") usually inherited together.

Molecular HLA typing methods rely on amplifying sufficient copies of HLA sequences by the polymerase chain reaction (PCR) or other suitable technique. PCR amplification for HLA typing can be locus-, allele group-, or allele-specific depending on the technique in use. The amplicons are further tested to detect specific polymorphic sequences, such as those that define specific HLA alleles or groups of related alleles that encode a specific HLA antigen.

Polymorphism in HLA molecules occurs largely in the protein domains that comprise the peptide binding regions. For HLA class I molecules, DNA typing methods focus on exons 2 and 3, which encode the 1 and 2 domains of the HLA-A, B, and Cw heavy chains. For class II molecules, the peptide binding site is comprised of the first domains of the alpha and beta chains which are encoded by exon 2 of their respective genes.

For HLA-DR, only the beta chain is polymorphic. Therefore, DR typing schemes generally concentrate on exon 2 of the DRB1, DRB3, DRB4, and DRB5 genes. It should be noted that alleles of the DRB1 locus encode the serologically defined DR antigens 1-18, while the DRB3-5 loci encode DR52, DR53, and DR51 antigens, respectively. All individuals carry the DRB1 gene, but the presence of the DRB3-5 genes varies with specific haplotypes carrying different DRB1 genes. Therefore, individuals can have as few as one DR antigen (if they are homozygous for DR1, 8 or 10) or as many as four DR antigens (e.g., DR15, DR17, DR51, DR52). Additional attention has focused on HLA-DQ and DP antigens in recent years, due to reports of HLA antibodies specific for both alpha and beta chains. Consequently, complete typing for HLA-DQ and DP must also consider exon 2 of the polymorphic alpha chain.

Kits

The present invention provides kits for identifying a transplant donor for a recipient. Such kits may be suitable for the detection of nucleic acid species, or alternatively, may be for detection of a polypeptide gene product.

For detection of nucleic acids, such kits may contain a first container such as a vial or plastic tube or a microtiter plate that contains one or more oligonucleotide probes. The kits may optionally contain a second container that holds primers. The probe may be hybridisable to DNA comprising a single nucleotide polymorphism locus, or contain multiple probes that are capable of hybridizing to multiple single nucleotide polymorphism loci. Kits that contain an oligonucleotide probe immobilized on a solid support could also be developed, for example, using arrays.

For PCR amplification of nucleic acid, nucleic acid primers may be included in the kit that are complementary to at least a portion of a nucleic acid comprising a single nucleotide polymorphism locus. The set of primers typically includes at least two oligonucleotides that are capable of specific amplification of DNA. Fluorescent labeled oligonucleotides that will allow quantitative PCT determination may be included (e.g., TaqMan chemistry, Molecular Beacons). Suitable enzymes for DNA amplification may also be included.

Control nucleic acid may be included with the kit for the purposes of comparison or validation.

EXAMPLES

Example 1. Ancestral Haplotype Specificity of SNPs in the C4 Gene

Figure 2:
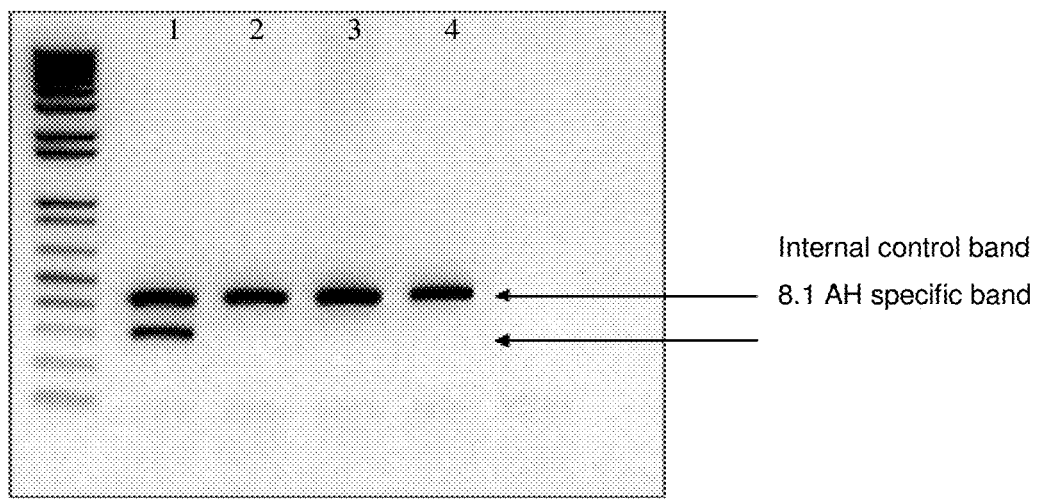
FIG. 2. Gel image of a PCR-SSP test for the detection of the 8.1 Ancestral Haplotype (AH) specific SNP pair found in the complement C4 gene. Sample 1 has the alpha, beta and delta block markers of the 8.1 AH and has a positive test for the gamma block SNP markers. Samples 2, 3 and 4 do not have any markers of the 8.1 AH and are negative for the SSP test for the gamma block SNP markers. HLA Types for samples.

Sequence specific primers (SSP) were used to detect the 8.1 Ancestral Haplotype (AH) specific SNP pairs in the complement C4 gene (FIG. 2). Sample 1 has the alpha, beta and delta block markers of the 8.1 AH and has a positive test for the gamma block SNP markers. Samples 2, 3 and 4 do not have any markers of the 8.1 AH and are negative for the SSP test for the gamma block SNP markers.

The Table in FIG. 3 shows that many samples with identical C4 allotypes have a different SNP profile. Some of the SNPs are found on a variety of samples and some appear unique to a sample (Ancestral Haplotype). This data suggests that the SNP profiles are markers for the Gamma block of the MHC ancestral haplotype and not the allotype of the sample. Gamma-Type Assay #8 and #15 are control SSP assays for C4A and C4B and are not listed.

Example 2. Exemplary PCR Typing Kit

The present inventors have developed a PCT assay kit for matching of patients and donors to reduce the risk of severe acute Graft-versus host disease. The PCR kit comprises 26 mixes containing PCR buffer, dNTPs, MgCl$_2$ and sequence specific primers, as well as a single vial of DNA polymerase. Each of the mixes for amplifying the C4 gene single nucleotide polymorphisms is provided in a single vial of 880 µl. The single nucleotide polymorphisms to be amplified in the assay are one or more of: A13189, T14952, G12749, A13950-A14483, G12071, A11483, T9763, A12152, A14831, T14757, C16954, T9881, C9796, A12568-A12837, T19588, T10289, A11437, T14563, A20170, T17316, C10676, G15108, T10309, and/or C13193. The assay kit further comprises control mixes for amplifying C4A and C4B gene internal fragments.

Preferably, the DNA sample to be tested in the assay kit is high molecular weight human genomic DNA at a concentration range of 20-100 ng/µl in Tris/EDTA buffer and OD$_{260/280}$>1.8, and which has been extracted from ACD or EDTA anticoagulated whole blood specimens.

PCR Assay Steps
1. All PCR assay mixes are set up for each sample to be tested.
2. The assay mixes are quickly thawed at room temperature. Once thawed, the mixes are vortexed briefly.
3. 7.85 µl of each mix is added into the reaction wells. 7.85 µl is added to a no amplification control well for each sample to be tested.
4. A mixture of DNA (64 µl) and DNA polymerase (4.8 µl) is prepared for each sample to be typed in the assay.
5. 2.15 µl of the DNA/polymerase mixture is dispensed into each reaction well.
6. The reaction wells are sealed and mixed gently by vortexing and brief centrifugation.
7. The reaction wells are placed in a thermal cycler and subject to the following amplification conditions:

| | |
|---|---|
| 95° C. - 10 mins | |
| 96° C. - 20 secs | |
| 60° C. - 30 secs | 33 cycles |
| 72° C. - 3 mins | |
| 15° C. - hold | |

Upon completion of the PCR, the amplification plate is removed from the thermal cycler and either processed directly to gel electrophoresis or stored at 4° C. until required.

Agarose Gel Electrophoresis and Interpretation
1. Amplification of the internal control and the target amplicons is confirmed by agarose gel electrophoresis using 2 µl of each PCR product combined with 5 µl of loading buffer (alternative volumes can be used). The use of 1% agarose gels is recommended.
2. There must be no PCR products in the no amplification control for each sample tested. If a band is evident, contamination may have occurred at some level and the run must be repeated.
3. All negative reactions should amplify the internal control amplicon.
4. All positive sequence specific PCRs (SSP) will result in the amplification of the target amplicon. The expected sizes of the amplicons are listed in Table 1.

TABLE 1

Expected amplification product sizes.

| Reaction No. | Reaction Mix | SSP Target Amplicon Size | Internal Control Amplicon Size |
|---|---|---|---|
| 1 | A13189 | ≈250 bp | ≈450 bp |
| 2 | T14952 | ≈360 bp | ≈300 bp |
| 3 | G12749 | ≈500 bp | ≈300 bp |
| 4 | C4B | ≈550 bp | ≈300 bp |
| 5 | C4A | ≈550 bp | ≈300 bp |
| 6 | A13950-A14483 | ≈500 bp | ≈300 bp |
| 7 | G12071 | ≈250 bp | ≈450 bp |
| 8 | A11483 | ≈200 bp | ≈450 bp |
| 9 | T9763 | ≈350 bp | ≈450 bp |
| 10 | A12152 | ≈200 bp | ≈450 bp |
| 11 | A14831 | ≈250 bp | ≈450 bp |
| 12 | T14757 | ≈350 bp | ≈300 bp |
| 13 | C16954 | ≈250 bp | ≈450 bp |
| 14 | T9881 | ≈250 bp | ≈450 bp |
| 15 | C9796 | ≈180 bp | ≈450 bp |
| 16 | A12568-A12837 | ≈300 bp | ≈450 bp |
| 17 | T19588 | ≈320 bp | ≈450 bp |
| 18 | T10289 | ≈200 bp | ≈450 bp |
| 19 | A11437 | ≈500 bp | ≈300 bp |
| 20 | T14563 | ≈500 bp | ≈300 bp |
| 21 | A20170 | ≈500 bp | ≈300 bp |
| 22 | T17316 | ≈350 bp | ≈450 bp |
| 23 | C10676 | ≈300 bp | ≈450 bp |
| 24 | G15108 | ≈450 bp | ≈300 bp |
| 25 | T10309 | ≈500 bp | ≈300 bp |
| 26 | C13193 | ≈250 bp | ≈450 bp |
| 27 | No Amp. Control | No Amp. | No Amp. |

Example 3. Matching Patients for Gamma-Type (SNPs)

Patients and donors were typed for the panel of SNPs using the PCR-SSP assay. Patient/Donor pairs were defined as mismatched if either the donor or patient was positive for at least one SNP from the panel of 26 SNPs, and the corresponding donor/patient was not (FIG. 4 and FIG. 5). FIG. 4 shows that Gamma-Type Mismatching results in an increased risk of severe aGVHD. Patients (x) matched (M) and mismatched (MM) for Gamma-Type and whether the patient was diagnosed with Acute GVHD and Acute GVHD grade. FIG. 5 shows that Gamma-Type Matching results in improved chances of long-term survival.

Example 4. Further Example of Gamma-Type PCR Typing Kit

The present inventors have developed a further PCT assay kit for matching of patients and donors to reduce the risk of severe acute GVHD. The PCR kit comprises 25 mixes containing PCR buffer, dNTPs, MgCl$_2$ and sequence specific primers, a no amplification control mix, and a single vial of DNA polymerase. Each of the mixes for amplifying the C4 gene single nucleotide polymorphisms is provided in an individual well of a 32 well plate. The single nucleotide polymorphisms to be amplified in the assay are one or more of: A13189, T14952, G12749, G12071, A11483, T9763, A12152, A14831, T14757, C16954, T9881, C9796, A12568-A12837, T19588, T10289, A11437, T14563, A20170, T17316, C10676, G15108, T10309, and/or C13193. The assay kit further comprises control mixes for amplifying C4A and C4B gene internal fragments.

Preferably, the DNA sample to be tested in the assay kit is high molecular weight human genomic DNA at a concentration range of 20-100 ng/µl in Tris/EDTA buffer and OD$_{260/280}$>1.8, and which has been extracted from ACD or EDTA anticoagulated whole blood specimens.

Procedure
1. PCR Set-Up
    1.1 Each 32-well reaction plate contains enough Gamma-Type mix for a single sample. Quickly thaw the Gamma-Type mixes/reaction plate at room temperature. Once thawed, vortex briefly and spin the 32-well plate to ensure all mixes are brought down to the bottom of the wells.
    1.2 Prepare a mixture of genomic DNA and DNA Polymerase (DNA POL-GAMMA-TYPE) for each sample to be typed according to Table 2 below. This should be prepared fresh for every new PCR. Pulse vortex the solution 3-4 times to mix.

TABLE 2

| Composition of the DNA/polymerase mixture required per sample | |
|---|---|
| Reagent | Volume |
| Genomic DNA | 57.5 µL |
| DNA POL - GAMMA-Type | 2.5 µL |

1.3 2 µL of the DNA/polymerase mixture is dispensed into each reaction well. The reaction wells are sealed, and mixed gently. The reaction wells are centrifuged briefly.
    1.4 The reaction wells are placed into a thermal cycler and amplified according to the thermal cycling conditions below:

| | |
|---|---|
| 95° C. - 10 mins | |
| 96° C. - 20 secs | |
| 61° C. - 30 secs | 28 cycles |
| 72° C. - 3 mins | |
| 96° C. - 20 secs | |

-continued

| | |
|---|---|
| 56° C. - 30 secs | 5 cycles |
| 72° C. - 3 mins | |
| 15° C. - hold | |

1.5 Amplification takes approximately 2.5 hours to complete. When the PCR is complete, the plate is removed from the thermal cycler and products analysed directly by gel electrophoresis or stored at 4° C. until required.
2. Agarose Gel Electrophoresis and Interpretation
    2.1 Amplification of the internal control and the target amplicons are confirmed by agarose gel electrophoresis using 2 µL of each PCR product combined with 5 µL of loading buffer (alternative volumes of loading buffer should be validated prior to use). The use of 2% agarose gels is recommended.
    2.2 There must be no PCR products in the negative control well (mix 26) for each sample tested. If a band is evident contamination may have occurred at some level and the run must be repeated.
    2.3 All negative Gamma-Type reactions should amplify the internal control amplicon. If neither the target, nor internal control amplicon are evident, the reaction cannot be interpreted and a failure (0) should be recorded on the relevant Gamma-Type worksheet.
    2.4 A positive Gamma-Type reaction is observed and recorded when the target amplicon is amplified. The expected size of each target amplicon is checked against Table 1 when scoring the reactions. Positive reactions may have a strong target amplicon present with a very weak or absent internal control. This is an acceptable positive reaction. When scoring reactions, record results using the number '1' for negative reactions and '2' for positive reactions. Any failed reactions (as described in point 2.3) should be recorded as '0'.
    2.5 Patient Gamma-Type profiles may be compared with donor Gamma-Type profiles to assist in the prediction of gamma block matching. In order to do this, pertinent sample information including the Name, Sample ID and DNA concentration, should be recorded for each patient and potential donor tested in a worksheet. Copies of the Gamma-Type gel images may be imported into the worksheet. The gel image can then be interpreted by scoring positive reactions where the target band is present with "2" and negative reactions where only the internal control band is present with "1". Failed or 'no amplification' reactions, where both the target and internal control are absent, are scored with a "0". These results should be entered in the worksheet for the patient and donors.
    2.6 Once all results have been entered and scored, the results are compared to see if any of the donors typed/entered are Gamma-Type matched to the patient. If contamination is detected or any reactions fail, the tests may need to be repeated.

FIG. 6 shows Gamma-Type PCR SSP analysis for both Gamma-Type matched (A) and mismatched (B) individuals.

Example 5. Gamma-Type Retrospective Study

A retrospective study was performed on 225 unrelated hematopoietic stem cell transplant (HSCT) donor-recipient pairs, from transplants performed from 1996-2005 in three Brazilian centres. Each individual in the transplant pairs was HLA typed (A,B,C,DRB1,DQB1) using Luminex technology. Gamma-Type assay was performed with 23 SNPs by PCR-SSP analysis, plus the C4A and C4B isotype specific SNPs. A Gamma-Type match was recorded where there was a complete match in the Gamma-Type SNP profile in a transplant/recipient pair. A Gamma-Type mismatch was recorded where there was a difference of at least 1 SNP in the SNP profile.

Analysis of the HLA types and Gamma-Type profiles demonstrated that HLA mismatched pairs are more likely to be Gamma-Type mismatched (Table 3).

TABLE 3

HLA mismatched pairs more likely to be Gamma-Type Mismatched

|  | GT Matched | GT Mismatched |
| --- | --- | --- |
| HLA 9/10 Matched | 16 (21%) | 61 (79%) |
| HLA 10/10 Matched | 77 (52%) | 71 (48%) |

Chi Square p < 0.001

In addition, the present inventors found Gamma-Type matching in 10/10 HLA matched pairs reduces the risk of cGvHD and Grade III/IV aGvHD (FIG. 7). Gamma-Type matching in 9/10 HLA matched pairs was shown to significantly improve survival, which may be a result of balancing disease relapse and GvHD. In this respect, the inventors found that the survival rates of Gamma-Type matched, HLA 9/10 matched patients exceeded Gamma-Type matched and HLA 10/10 matched patients.

In summary, the present inventors determined that non-HLA genomic sequence impacted the outcome of unrelated hematopoietic stem cell transplant. This suggests that Gamma-Type matching and high resolution HLA typing result in matching of non-HLA loci critical for the outcome of hematopoietic stem cell transplant. Hence, the Gamma-Type assay of the present invention can be used to identify the best donor for improved outcomes following unrelated HSCT.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2013903971, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Fernando et al. (2010) Hum Mutat, 31(7):866-874
Metzker (2010) Nat Rev Genet, 11(1):31-46
Petersdorf et al. (2007) PLoS Med, 4(1): e8
Shen et al. (2013) Genome Medicine, 5:50

The invention claimed is:

1. A method of matching a transplant donor with a transplant recipient, comprising:
   (a) determining the presence or absence of a single nucleotide polymorphism (SNP) in a C4 gene in a transplant donor nucleic acid sample;
   (b) determining the presence or absence of a SNP in a C4 gene in a transplant recipient nucleic acid sample, wherein determining the presence or absence of the SNP comprises hybridizing a SNP primer to the transplant donor nucleic acid sample or to the transplant recipient nucleic acid sample, wherein the SNP primer comprises the nucleotide sequence of SEQ ID NO: 29 or 30; and
   (c) matching the transplant donor with the transplant recipient, wherein the presence of the same SNP in the C4 gene is found in the transplant donor nucleic acid sample and the transplant recipient nucleic acid sample.

2. The method of claim 1, further comprising determining the presence or absence of at least 5 different SNPs in the C4 gene in the transplant donor nucleic acid sample and in the transplant recipient nucleic acid sample.

3. The method of claim 1, wherein determining the presence or absence of a SNP comprises hybridizing a SNP primer to the donor nucleic acid sample and to the recipient nucleic acid sample.

4. The method of claim 1, further comprising hybridizing an additional SNP primer to the transplant donor nucleic acid sample or to the transplant recipient nucleic acid sample, wherein the additional SNP primer comprises a nucleotide sequence selected from any one of SEQ ID NOs: 05-28 and 31-50.

5. The method of claim 1, wherein the SNP primer is in solution.

6. The method of claim 1, wherein the SNP primer is attached to a substrate.

7. The method of claim 1, further comprising hybridizing a control primer to the transplant donor nucleic acid sample or to the transplant recipient nucleic acid sample.

8. The method of claim 7, wherein the control primer specifically hybridizes to a C4 gene isoform selected from a C4A isoform or a C4B isoform.

9. The method of claim 7, wherein the control primer specifically hybridizes to the C4A isoform.

10. The method of claim 7, wherein the control primer comprises a nucleotide sequence selected from SEQ ID NO: 03 and 04.

11. The method of claim 1, further comprising:
    transplanting a tissue from the transplant donor to the transplant recipient.

12. A method of matching a transplant donor with a transplant recipient, comprising:
    (a) determining the presence or absence of a single nucleotide polymorphism (SNP) in a C4 gene in a transplant donor nucleic acid sample;
    (b) determining the presence or absence of a SNP in a C4 gene in a transplant recipient nucleic acid sample, wherein determining the presence or absence of a SNP comprises hybridizing a SNP primer comprising the nucleotide sequence of SEQ ID NO: 29 or 30 to the transplant donor nucleic acid sample or to the transplant recipient nucleic acid sample; and
    (c) matching the transplant donor with the transplant recipient, wherein the presence or absence of the same SNP in the C4 gene is found in the transplant donor nucleic acid sample and the transplant recipient nucleic acid sample.

13. The method of claim 12, further comprising hybridizing an additional SNP primer to the transplant donor nucleic acid sample or to the transplant recipient nucleic acid sample, wherein the additional SNP primer comprises a nucleotide sequence selected from any one of SEQ ID NOs: 05-28, and 31-50.

14. The method of claim 13, wherein the additional SNP primer comprises a nucleotide sequence selected from any one of SEQ ID NOs: 05, 09, 12, 13, 16, 17, 19, 22, 24, 25, 31, 33, 35, 37, 39, 41, 44, 46, 47, and 50.

15. The method of claim 12, wherein the SNP primer is in solution.

16. The method of claim 12, wherein the SNP primer is attached to a substrate.

17. The method of claim 12, further comprising hybridizing a control primer to the transplant donor nucleic acid sample or to the transplant recipient nucleic acid sample.

18. The method of claim 17, wherein the control primer specifically hybridizes to a C4 gene isoform selected from a C4A isoform or a C4B isoform.

19. The method of claim 17, wherein the control primer comprises a nucleotide sequence selected from SEQ ID NO: 03 and 04.

* * * * *

SEQUENCE LISTING

```
<160> NUMBER OF SEQ ID NOS: 50

<210> SEQ ID NO 1
<211> LENGTH: 6
<212> TYPE: PRT
<213> ORGANISM: Homo sapiens

<400> SEQUENCE: 1

Pro Cys Pro Val Leu Asp
1               5

<210> SEQ ID NO 2
<211> LENGTH: 6
<212> TYPE: PRT
<213> ORGANISM: Homo sapiens

<400> SEQUENCE: 2

Leu Ser Pro Val Ile His
1               5

<210> SEQ ID NO 3
<211> LENGTH: 19
<212> TYPE: DNA
<213> ORGANISM: Artificial Sequence
<220> FEATURE:
<223> OTHER INFORMATION: C4A control forward primer

<400> SEQUENCE: 3
gacccctgtc cagtgttag                                                19

<210> SEQ ID NO 4
```

```
<211> LENGTH: 20
<212> TYPE: DNA
<213> ORGANISM: Artificial Sequence
<220> FEATURE:
<223> OTHER INFORMATION: C4A control reverse primer

<400> SEQUENCE: 4
cctcctctga gtcttcatcc                                              20

<210> SEQ ID NO 5
<211> LENGTH: 23
<212> TYPE: DNA
<213> ORGANISM: Artificial Sequence
<220> FEATURE:
<223> OTHER INFORMATION: T9763 forward primer

<400> SEQUENCE: 5
ccccgggttt ctgtctatag agt                                          23

<210> SEQ ID NO 6
<211> LENGTH: 20
<212> TYPE: DNA
<213> ORGANISM: Artificial Sequence
<220> FEATURE:
<223> OTHER INFORMATION: T9763 reverse primer

<400> SEQUENCE: 6
tgccaggtga tggtccacaa                                              20

<210> SEQ ID NO 7
<211> LENGTH: 19
<212> TYPE: DNA
<213> ORGANISM: Artificial Sequence
<220> FEATURE:
<223> OTHER INFORMATION: C9796 forward primer

<400> SEQUENCE: 7
tcctcgtgtt ggggacacc                                               19

<210> SEQ ID NO 8
<211> LENGTH: 21
<212> TYPE: DNA
<213> ORGANISM: Artificial Sequence
<220> FEATURE:
<223> OTHER INFORMATION: C9796 reverse primer

<400> SEQUENCE: 8
agagtggttg cctcttcatg g                                            21

<210> SEQ ID NO 9
<211> LENGTH: 24
<212> TYPE: DNA
<213> ORGANISM: Artificial Sequence
<220> FEATURE:
<223> OTHER INFORMATION: T9881 forward primer

<400> SEQUENCE: 9
caggacattc agcaaaacac cgat                                         24

<210> SEQ ID NO 10
<211> LENGTH: 20
<212> TYPE: DNA
<213> ORGANISM: Artificial Sequence
<220> FEATURE:
<223> OTHER INFORMATION: T9881 reverse primer

<400> SEQUENCE: 10
```
gcctggctat cgctggatgt                                              20

<210> SEQ ID NO 11
<211> LENGTH: 21
<212> TYPE: DNA
<213> ORGANISM: Artificial Sequence
<220> FEATURE:
<223> OTHER INFORMATION: T10289 forward primer

<400> SEQUENCE: 11
ccaactccct gcgagtggat g                                            21

<210> SEQ ID NO 12
<211> LENGTH: 18
<212> TYPE: DNA
<213> ORGANISM: Artificial Sequence
<220> FEATURE:
<223> OTHER INFORMATION: T10289 reverse primer

<400> SEQUENCE: 12
ctccagctgg cagggca                                                 18

<210> SEQ ID NO 13
<211> LENGTH: 20
<212> TYPE: DNA
<213> ORGANISM: Artificial Sequence
<220> FEATURE:
<223> OTHER INFORMATION: T10309 forward primer

<400> SEQUENCE: 13
ctctcccact ctgacctcct                                              20

<210> SEQ ID NO 14
<211> LENGTH: 21
<212> TYPE: DNA
<213> ORGANISM: Artificial Sequence
<220> FEATURE:
<223> OTHER INFORMATION: T10309 reverse primer

<400> SEQUENCE: 14
ggaacacctg aagggcactg t                                            21

<210> SEQ ID NO 15
<211> LENGTH: 20
<212> TYPE: DNA
<213> ORGANISM: Artificial Sequence
<220> FEATURE:
<223> OTHER INFORMATION: C10676 forward primer

<400> SEQUENCE: 15
acatgtccca cgtcctctcc                                              20

<210> SEQ ID NO 16
<211> LENGTH: 19
<212> TYPE: DNA
<213> ORGANISM: Artificial Sequence
<220> FEATURE:
<223> OTHER INFORMATION: C10676 reverse primer

<400> SEQUENCE: 16
atccttggct ggaagctcg                                               19

<210> SEQ ID NO 17
<211> LENGTH: 20
<212> TYPE: DNA

<210> SEQ ID NO 17
<211> LENGTH: 20
<212> TYPE: DNA
<213> ORGANISM: Artificial Sequence
<220> FEATURE:
<223> OTHER INFORMATION: A11437 forward primer

<400> SEQUENCE: 17
gacacgtctg cccatgatga                                          20

<210> SEQ ID NO 18
<211> LENGTH: 20
<212> TYPE: DNA
<213> ORGANISM: Artificial Sequence
<220> FEATURE:
<223> OTHER INFORMATION: A11437 reverse primer

<400> SEQUENCE: 18
ggcccagaca gggtgacatc                                          20

<210> SEQ ID NO 19
<211> LENGTH: 17
<212> TYPE: DNA
<213> ORGANISM: Artificial Sequence
<220> FEATURE:
<223> OTHER INFORMATION: A11483 forward primer

<400> SEQUENCE: 19
cagcagccgg actgcca                                             17

<210> SEQ ID NO 20
<211> LENGTH: 22
<212> TYPE: DNA
<213> ORGANISM: Artificial Sequence
<220> FEATURE:
<223> OTHER INFORMATION: A11483 reverse primer

<400> SEQUENCE: 20
aggtcctcct cctgcaggat ct                                       22

<210> SEQ ID NO 21
<211> LENGTH: 20
<212> TYPE: DNA
<213> ORGANISM: Artificial Sequence
<220> FEATURE:
<223> OTHER INFORMATION: G12071 forward primer

<400> SEQUENCE: 21
cactgtggct ccccgactct                                          20

<210> SEQ ID NO 22
<211> LENGTH: 20
<212> TYPE: DNA
<213> ORGANISM: Artificial Sequence
<220> FEATURE:
<223> OTHER INFORMATION: G12071 reverse primer

<400> SEQUENCE: 22
tcagtctgcc tctgccctcc                                          20

<210> SEQ ID NO 23
<211> LENGTH: 20
<212> TYPE: DNA
<213> ORGANISM: Artificial Sequence
<220> FEATURE:
<223> OTHER INFORMATION: A12152 forward primer

<400> SEQUENCE: 23
tgggcacagt ggcagagatt                                          20

-continued

<210> SEQ ID NO 24
<211> LENGTH: 20
<212> TYPE: DNA
<213> ORGANISM: Artificial Sequence
<220> FEATURE:
<223> OTHER INFORMATION: A12512 reverse primer

<400> SEQUENCE: 24
tgtctgggcc tcaggtgacc                                          20

<210> SEQ ID NO 25
<211> LENGTH: 15
<212> TYPE: DNA
<213> ORGANISM: Artificial Sequence
<220> FEATURE:
<223> OTHER INFORMATION: A12568 - A12837 forward primer

<400> SEQUENCE: 25
tgcccacgga agcca                                               15

<210> SEQ ID NO 26
<211> LENGTH: 21
<212> TYPE: DNA
<213> ORGANISM: Artificial Sequence
<220> FEATURE:
<223> OTHER INFORMATION: A12568 - A12837 reverse primer

<400> SEQUENCE: 26
ctacagcctg cccttctagc a                                        21

<210> SEQ ID NO 27
<211> LENGTH: 20
<212> TYPE: DNA
<213> ORGANISM: Artificial Sequence
<220> FEATURE:
<223> OTHER INFORMATION: G12479 forward primer

<400> SEQUENCE: 27
ggccaggtgc ccaacagccg                                          20

<210> SEQ ID NO 28
<211> LENGTH: 20
<212> TYPE: DNA
<213> ORGANISM: Artificial Sequence
<220> FEATURE:
<223> OTHER INFORMATION: G12749 reverse primer

<400> SEQUENCE: 28
ggccaggtgc ccaacagccg                                          20

<210> SEQ ID NO 29
<211> LENGTH: 21
<212> TYPE: DNA
<213> ORGANISM: Artificial Sequence
<220> FEATURE:
<223> OTHER INFORMATION: A13189 forward primer

<400> SEQUENCE: 29
gccaccttcg gattgatgtg a                                        21

<210> SEQ ID NO 30
<211> LENGTH: 20
<212> TYPE: DNA
<213> ORGANISM: Artificial Sequence
<220> FEATURE:

<223> OTHER INFORMATION: A13189 reverse primer

<400> SEQUENCE: 30
cagcctcgag gaagcctcaa                                                   20

<210> SEQ ID NO 31
<211> LENGTH: 20
<212> TYPE: DNA
<213> ORGANISM: Artificial Sequence
<220> FEATURE:
<223> OTHER INFORMATION: C13193 forward primer

<400> SEQUENCE: 31
cttcggattc atgtgggacc                                                   20

<210> SEQ ID NO 32
<211> LENGTH: 20
<212> TYPE: DNA
<213> ORGANISM: Artificial Sequence
<220> FEATURE:
<223> OTHER INFORMATION: C13193 reverse primer

<400> SEQUENCE: 32
cttggtctcg ggaggcagtg                                                   20

<210> SEQ ID NO 33
<211> LENGTH: 20
<212> TYPE: DNA
<213> ORGANISM: Artificial Sequence
<220> FEATURE:
<223> OTHER INFORMATION: T14563 forward primer

<400> SEQUENCE: 33
ggtgaggggt gaggggctct                                                   20

<210> SEQ ID NO 34
<211> LENGTH: 20
<212> TYPE: DNA
<213> ORGANISM: Artificial Sequence
<220> FEATURE:
<223> OTHER INFORMATION: T14563 reverse primer

<400> SEQUENCE: 34
cccttggtct gaggactacc                                                   20

<210> SEQ ID NO 35
<211> LENGTH: 20
<212> TYPE: DNA
<213> ORGANISM: Artificial Sequence
<220> FEATURE:
<223> OTHER INFORMATION: T14757 forward primer

<400> SEQUENCE: 35
ccctgccttc ctgtttactt                                                   20

<210> SEQ ID NO 36
<211> LENGTH: 20
<212> TYPE: DNA
<213> ORGANISM: Artificial Sequence
<220> FEATURE:
<223> OTHER INFORMATION: T14757 reverse primer

<400> SEQUENCE: 36
cccttggtct gaggactacc                                                   20

```
<210> SEQ ID NO 37
<211> LENGTH: 20
<212> TYPE: DNA
<213> ORGANISM: Artificial Sequence
<220> FEATURE:
<223> OTHER INFORMATION: A14831 forward primer

<400> SEQUENCE: 37
atgccgtgtc gcccatccca                                              20

<210> SEQ ID NO 38
<211> LENGTH: 20
<212> TYPE: DNA
<213> ORGANISM: Artificial Sequence
<220> FEATURE:
<223> OTHER INFORMATION: A14831 reverse primer

<400> SEQUENCE: 38
cccttggtct gaggactacc                                              20

<210> SEQ ID NO 39
<211> LENGTH: 20
<212> TYPE: DNA
<213> ORGANISM: Artificial Sequence
<220> FEATURE:
<223> OTHER INFORMATION: T14592 forward primer

<400> SEQUENCE: 39
agagatggca gaccaggctt                                              20

<210> SEQ ID NO 40
<211> LENGTH: 20
<212> TYPE: DNA
<213> ORGANISM: Artificial Sequence
<220> FEATURE:
<223> OTHER INFORMATION: T14952 reverse primer

<400> SEQUENCE: 40
agtggttcac cagggagtgg                                              20

<210> SEQ ID NO 41
<211> LENGTH: 21
<212> TYPE: DNA
<213> ORGANISM: Artificial Sequence
<220> FEATURE:
<223> OTHER INFORMATION: G15108 forward primer

<400> SEQUENCE: 41
tgccctgtct gcctactgga t                                            21

<210> SEQ ID NO 42
<211> LENGTH: 18
<212> TYPE: DNA
<213> ORGANISM: Artificial Sequence
<220> FEATURE:
<223> OTHER INFORMATION: G15108 reverse primer

<400> SEQUENCE: 42
ctcaaaacag ccgcaccc                                                18

<210> SEQ ID NO 43
<211> LENGTH: 20
<212> TYPE: DNA
<213> ORGANISM: Artificial Sequence
<220> FEATURE:
<223> OTHER INFORMATION: C16954 forward primer
```

<400> SEQUENCE: 43
acatgtccca cgtcctctcc                                          20

<210> SEQ ID NO 44
<211> LENGTH: 25
<212> TYPE: DNA
<213> ORGANISM: Artificial Sequence
<220> FEATURE:
<223> OTHER INFORMATION: C16954 reverse primer

<400> SEQUENCE: 44
catagtcctc atagtcctcg tttgg                                    25

<210> SEQ ID NO 45
<211> LENGTH: 20
<212> TYPE: DNA
<213> ORGANISM: Artificial Sequence
<220> FEATURE:
<223> OTHER INFORMATION: T17316 forward primer

<400> SEQUENCE: 45
ccagccaagg atgacccaga                                          20

<210> SEQ ID NO 46
<211> LENGTH: 17
<212> TYPE: DNA
<213> ORGANISM: Artificial Sequence
<220> FEATURE:
<223> OTHER INFORMATION: T17316 reverse primer

<400> SEQUENCE: 46
ggtcagcacg cagggca                                             17

<210> SEQ ID NO 47
<211> LENGTH: 20
<212> TYPE: DNA
<213> ORGANISM: Artificial Sequence
<220> FEATURE:
<223> OTHER INFORMATION: T19588 forward primer

<400> SEQUENCE: 47
ccctccctcg gggaccggct                                          20

<210> SEQ ID NO 48
<211> LENGTH: 21
<212> TYPE: DNA
<213> ORGANISM: Artificial Sequence
<220> FEATURE:
<223> OTHER INFORMATION: T19588 reverse primer

<400> SEQUENCE: 48
tcacacttcc agatggtcag g                                        21

<210> SEQ ID NO 49
<211> LENGTH: 21
<212> TYPE: DNA
<213> ORGANISM: Artificial Sequence
<220> FEATURE:
<223> OTHER INFORMATION: A20170 forward primer

<400> SEQUENCE: 49
tttgctctga caccaacttc c                                        21

<210> SEQ ID NO 50
<211> LENGTH: 20

```
<212> TYPE: DNA
<213> ORGANISM: Artificial Sequence
<220> FEATURE:
<223> OTHER INFORMATION: A20170 reverse primer

<400> SEQUENCE: 50
ggtcataggt ggccgcatct                                                     20
```